(12) United States Patent
Suzuki et al.

(10) Patent No.: US 12,053,195 B2
(45) Date of Patent: Aug. 6, 2024

(54) METHOD AND DEVICE OF INSERTING TREATMENT DEVICE INTO HOLLOW ORGAN

(71) Applicant: OLYMPUS MEDICAL SYSTEMS CORP., Tokyo (JP)

(72) Inventors: Takahiro Suzuki, Hachioji (JP); Tomofumi Katayama, Kunitachi (JP); Yutaka Yanuma, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 139 days.

(21) Appl. No.: 17/474,448

(22) Filed: Sep. 14, 2021

(65) Prior Publication Data
US 2022/0087695 A1    Mar. 24, 2022

Related U.S. Application Data

(60) Provisional application No. 63/080,089, filed on Sep. 18, 2020.

(51) Int. Cl.
| | |
|---|---|
| *A61B 17/221* | (2006.01) |
| *A61B 1/00* | (2006.01) |
| *A61B 1/01* | (2006.01) |
| *A61B 17/22* | (2006.01) |

(52) U.S. Cl.
CPC ........ *A61B 17/221* (2013.01); *A61B 1/00002* (2013.01); *A61B 1/00071* (2013.01); *A61B 1/01* (2013.01); *A61B 2017/22047* (2013.01); *A61B 2017/22051* (2013.01)

(58) Field of Classification Search
CPC .. A61M 25/09041; A61M 2025/09125; A61M 2025/09116
See application file for complete search history.

(56) References Cited

U.S. PATENT DOCUMENTS

| | | | |
|---|---|---|---|
| 2002/0095141 A1 | 7/2002 | Belef et al. | |
| 2003/0040769 A1 | 2/2003 | Kelley et al. | |
| 2004/0236351 A1* | 11/2004 | Yanuma | A61B 17/221 |
| | | | 606/127 |
| 2005/0075647 A1* | 4/2005 | Walters | A61M 25/104 |
| | | | 606/108 |

(Continued)

FOREIGN PATENT DOCUMENTS

WO    WO-2019113101 A1 *  6/2019 ........ A61M 25/0113

OTHER PUBLICATIONS

Extended European Search Report dated Feb. 15, 2022, issued in corresponding EP Patent Application No. 21196744.3.

*Primary Examiner* — Shaun L David
(74) *Attorney, Agent, or Firm* — Morgan, Lewis & Bockius LLP

(57) ABSTRACT

A guidewire holding device comprises a sheath including a lumen, a holder disposed at a distal end of the sheath and configured to be switchable between holding a guidewire and releasing the guidewire, a treatment tool inserted in the lumen to perform an intended treatment, and a wire connected to the treatment tool and configured to move the treatment tool between a first configuration and a second configuration. In the first configuration, the treatment tool is contained insider the lumen, and, in the second configuration, the treatment tool is protruded from the distal end of the sheath.

19 Claims, 18 Drawing Sheets

(56) References Cited

U.S. PATENT DOCUMENTS

| | | | |
|---|---|---|---|
| 2009/0171278 A1* | 7/2009 | Hirszowicz | A61M 25/104 |
| | | | 604/509 |
| 2012/0203066 A1* | 8/2012 | Okazaki | A61B 1/00154 |
| | | | 600/114 |
| 2016/0121084 A1 | 5/2016 | Yokota et al. | |
| 2019/0022353 A1* | 1/2019 | Khanicheh | A61M 25/0138 |
| 2019/0038376 A1* | 2/2019 | Yanuma | A61B 17/00234 |
| 2019/0365206 A1* | 12/2019 | Katayama | A61B 1/00133 |
| 2021/0085930 A1* | 3/2021 | Suzuki | A61M 25/09041 |

* cited by examiner

METHOD AND DEVICE OF INSERTING TREATMENT DEVICE INTO HOLLOW ORGAN

RELATED APPLICATION DATA

This application is based on and claims priority under 35 U.S.C. § 119 to U.S. Provisional Application No. 63/080,089, filed Sep. 18, 2020, the entire contents of which are incorporated herein by reference.

FIELD OF THE INVENTION

The present invention relates to a device and a method of inserting a medical treatment tool into a hollow organ of a subject (such as a patient) using a guidewire. In particular, the present invention relates to a guidewire holding device and a method of using the guidewire holding device to insert an endoscopic treatment tool into a hollow organ, such as the bile duct or the pancreatic duct, through an opening, such as the duodenal papilla.

DESCRIPTION OF THE RELATED ART

A method and a device of introducing a medical treatment tool into a human hollow organ using a guidewire for treatment and examination of the human hollow organ have been well known. When obstruction such as stenosis or occlusion occurs at an opening of the hollow organ, the guidewire itself cannot be inserted into the hollow organ. For example, when a duodenal papilla is tightly closed, it is difficult to insert the guidewire into a desired hollow organ such as a bile duct or a pancreatic duct via the duodenal papilla.

As a solution in such a situation, an endoscopic ultrasound guided rendezvous technique (EUS-RV) has been developed. In a typical EUS-RV, an operator inserts an ultrasound endoscope into the digestive track via the patient's mouth. The bile duct or the pancreatic duct is confirmed through an ultrasound image, so that a puncture needle is inserted into a channel of the ultrasonic endoscope and is punctured into the bile duct or the pancreatic duct. Then, the operator inserts a first guidewire into a lumen of the puncture needle and the distal end of the first guidewire is inserted from the lumen of the puncture needle into the bile duct or the pancreatic duct. Next, the operator pushes the first guidewire to cause the distal end of the first guidewire into the duodenum from the duodenal papilla. Thereafter, the ultrasonic endoscope and the puncture needle are removed from the body of the patient, e.g., by pulling out, while the distal end of the first guidewire is indwelt in the duodenum.

Next, the operator inserts an endoscope via the patient's mouth to the vicinity of the duodenal papilla of the duodenum. A guidewire grasping device is inserted into a channel of the endoscope so as to grasp and hold the first guidewire. While holding the first guidewire, the guidewire grasping device is pulled with respect to the endoscope, the distal end of the first guidewire is drawn into the channel of the endoscope, and is drawn out from the forceps port of the endoscope. Another catheter is inserted into the forceps port of the endoscope along the extracted first guidewire, and the tip of the catheter is inserted into the bile duct. A second guidewire is inserted into the bile duct through a lumen of the catheter.

When the second guidewire is endoscopically indwelt, the engagement of the guidewire grasping device with the first guidewire is released. The first guidewire is removed from the patient's body, and the guidewire grasping device are removed out to duodenum, leaving the second guidewire at the bile duct. When the above operations are completed, a treatment device is indwelt via the second guidewire to perform an endoscopic retrograde cholangiopancreatography (ERCP) procedure.

The conventional EUS-RV procedure, however, requires at least two guidewires to indwell the treatment device, and also requires to catch and release the first guidewire before performing the ERCP procedure. In order to conduct the treatment as soon as possible to reduce the burden on the patient, it has been a problem that the operation before the ERCP procedure is complicated and time-consuming.

SUMMARY OF THE INVENTION

Accordingly, the present disclosure is directed to a guidewire holding device and a method of using the guidewire holding device to insert a treatment tool, which substantially obviates one or more of the issues due to limitations and disadvantages of related EUS-RV device and method.

An object of the present disclosure is to provide a guidewire holding device comprises a sheath including a lumen, a holder disposed at a distal end of the sheath and configured to be switchable between holding a guidewire and releasing the guidewire, a treatment tool inserted in the lumen to perform an intended treatment, and a wire connected to the treatment tool and configured to move the treatment tool between a first configuration and a second configuration. In the first configuration, the treatment tool is contained insider the lumen, and, in the second configuration, the treatment tool is protruded from the distal end of the sheath.

Another object of the present disclosure is to provide a guidewire holding device comprising a sheath including a first lumen and a second lumen; a holder disposed at a distal end of the sheath and configured to be switchable between holding a guidewire and releasing the guidewire; an operation wire inserted in the first lumen and connected to the holder; a treatment tool mounted on the sheath and connected to the second lumen and operable to be switchable between a first configuration and a second configuration, wherein the treatment tool is a balloon and the second lumen is an air delivering lumen, in the first configuration, the balloon is not inflated by the air delivering lumen, and in the second configuration, the balloon is inserted into a target organ and is inflated by the air delivering lumen.

Still another object of the present disclosure is a method of using the guidewire holding device to insert a treatment tool into the body of a patient. The method comprises indwelling a guidewire at a bile duct and a duodenum through a duodenal papilla, inserting the treatment tool through a sheath of an endoscope into the duodenum, using a holder to connect the treatment tool to the guidewire in the duodenum, inserting the treatment tool into the bile duct along with the guidewire at a first status, switching the treatment tool from the first status into a second status, and performing a treatment after the switching of the treatment tool to the second status. In the first status, the treatment tool is contained inside the sheath; in the second status, the treatment tool is protruded from a distal end of the sheath.

Additional features and advantages will be set forth in the description that follows, and in part will be apparent from the description, or may be learned by practice of the invention. The objectives and other advantages of the disclosed input device will be realized and attained by the structure particularly pointed out in the written description and claims thereof as well as the appended drawings.

BRIEF DESCRIPTION OF THE DRAWING

The following detailed description of preferred embodiments can be read in connection with the accompanying drawings in which like numerals designate like elements and in which.

DETAILED DESCRIPTION

Various examples of a device and a method for inserting a medical treatment tool into a hollow organ of a subject (such as a patient) using a guidewire will be described with reference to the drawings.

Figure 1:
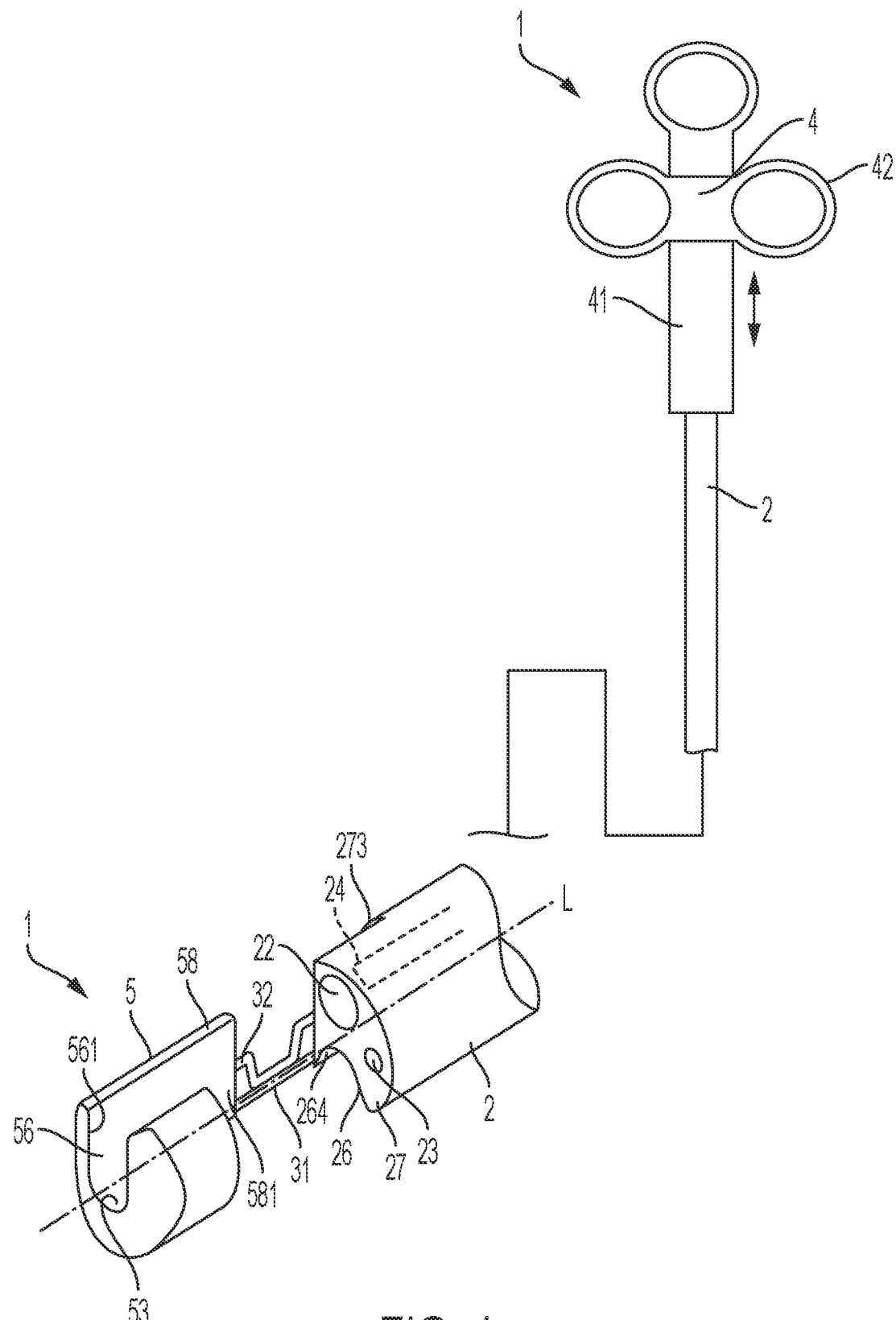
FIG. 1 is an exploded view schematically showing a guidewire holding device of an endoscope according to an exemplary embodiment.
Figure 2:
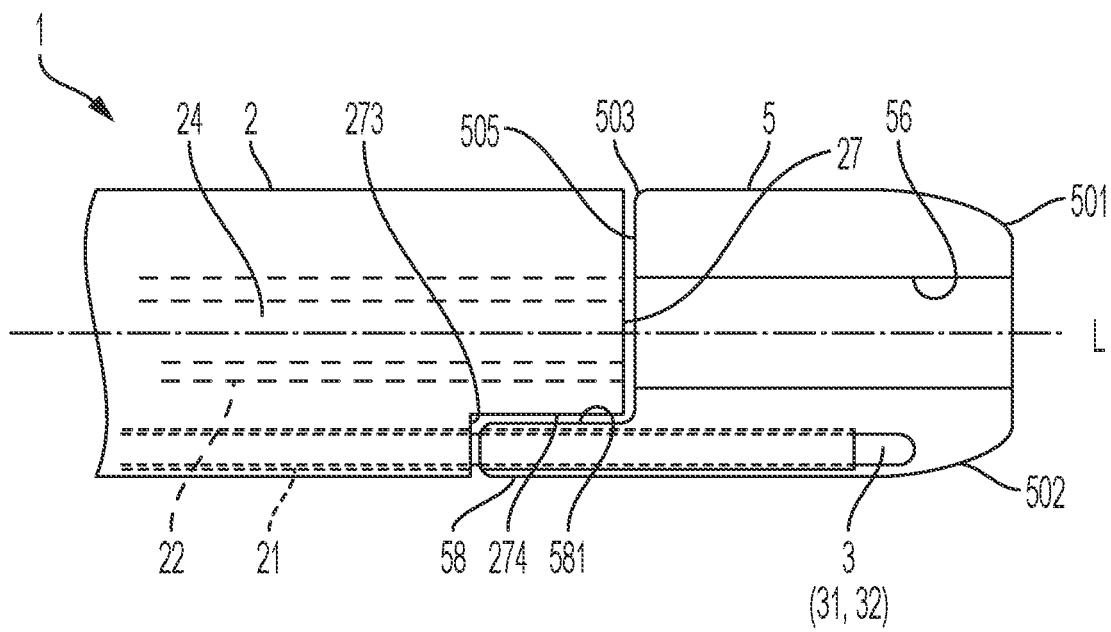
FIG. 2 is a top view schematically showing a distal end portion of the guidewire holding device of FIG. 1.
Figure 3:
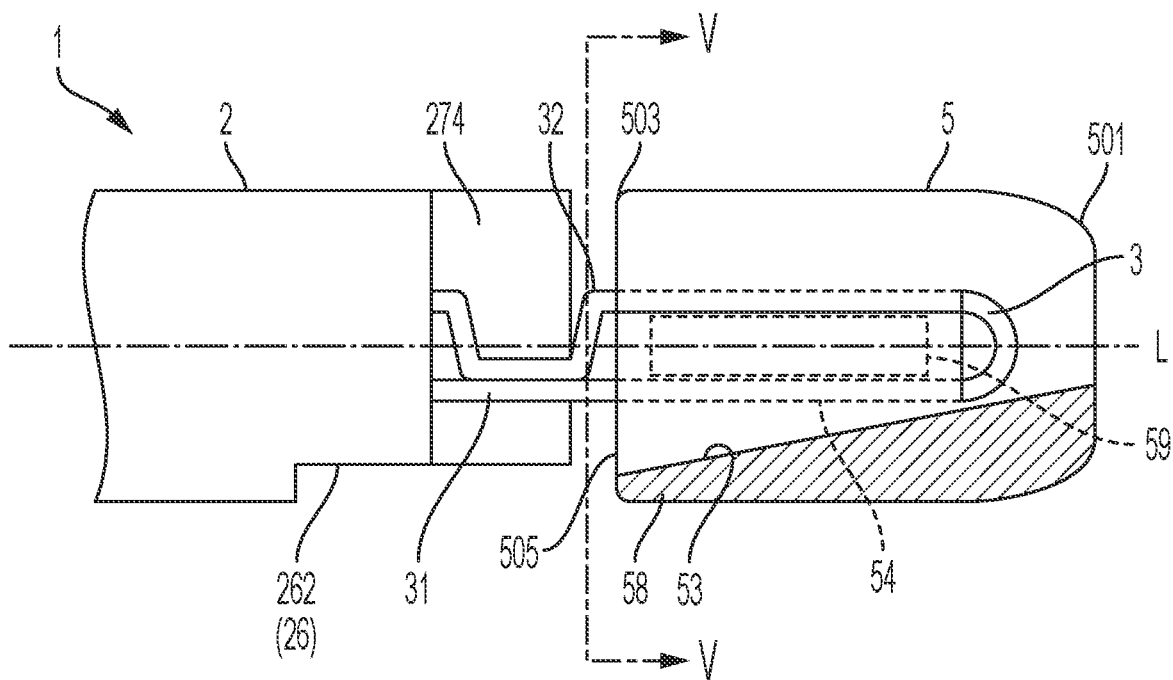
FIG. 3 is a side view schematically showing the distal end portion of the guidewire holding device of FIG. 1.

FIG. 1 is an overall view schematically showing a guidewire holding device 1 of an endoscope according to an exemplary embodiment. FIG. 2 is a top view schematically showing a distal end portion of the guidewire holding device 1 of FIG. 1. FIG. 3 is side view schematically showing the distal end portion of the guidewire holding device of FIG. 1.

As shown in FIG. 1, an endoscope includes the guidewire holding device 1 that is a capable of holding a medical guidewire used by being inserted into the body of a patient, and disposing a treatment device (tool) in a target lumen of a hollow organ during an EUS-RV procedure.

In this exemplary embodiment, the guidewire holding device 1 is configured as a combined device that combines a guidewire holder and a treatment tool into one device. The guidewire holding device 1 is disposed at or protruded from a distal end of an insertion portion of the endoscope.

As shown in FIGS. 1-4, the guidewire holding device 1 may include a sheath 2 inserted in the insertion portion of the endoscope, an operation wire 3 inside the sheath 2, a holder 5 connected to the operation wire 3, an operation unit 4 operating the guidewire holding device 1, and a treatment device 24 contained inside the sheath 2.

In the guidewire holding device 1, the holder 5 may advance and retract on a distal end side of the sheath 2 as the operation wire 3 advances and retracts, and as will be described later, a guidewire GW (in FIG. 6) positioned outside the sheath 2 can be captured and held by the holder 5.

The sheath 2 is a flexible long member. A proximal end portion of the sheath 2 is connected to an operation portion main body 41 of the operation unit 4 which is operated by an operator. The sheath 2 is inserted into the body of a patient via the insertion portion of the endoscope, and has a length such that the distal end portion of the sheath 2 can protrude from the insertion portion of the endoscope. The sheath 2 may include a plurality of lumens as shown in FIG. 1. In this exemplary embodiment, the sheath 2 includes a lumen 21 (in FIG. 2) extending in a longitudinal axis L direction, and a lumen 22 extending parallel to the lumen 21. The lumen 21 may be configured for inserting the operation wire 3, and the lumen 22 may be configured for inserting and storing the treatment device 24. The sheath 2 may have an additional lumen 23 (see FIGS. 7(A) and 7(B)) without increasing a diameter of the sheath 2. The lumens 21-23 may be different in size and shape from each other.

As will be described later, the guidewire holding device 1 may use the lumen 21 for the treatment device 24. In that situation, the treatment device 24 is connected to the holder 5, and functions as an operation wire or is further connected to the operation wire 3.

The sheath 2 includes a groove 26 formed in a part of its outer periphery. The part of the outer periphery of the groove 26 is formed in a concave shape. The groove 26 is formed to extend in the longitudinal axis L direction from the distal end of the sheath 2 to the proximal end side. The groove 26 has the same shape as the shape of a tip edge 261 (in FIG. 4) from the tip to the base end of the groove 26. The groove 26 may be formed over the entire length of the sheath 2, or may be formed in a region having a predetermined length from the distal end to the proximal end side, for example, only in a portion protruding from the distal end of the insertion portion of the endoscope.

As shown in FIG. 2, the sheath 2 includes a distal end surface 27, on which a step portion 273 is formed to be recessed toward the base end side. The operation wire 3 is inserted in the lumen 21, and advances and retracts through the step portion 273. The step portion 273 has a side surface 274 formed by cutting out in a plane shape along the longitudinal axis L. When the base end of the protrusion 58 is in contact with the step portion 273, a slight gap is preferably formed between the base end face 505 of the holder 5 (excluding the protrusion 58) and the distal end face 27 of the sheath 2. When the holder 5 and the sheath 2 are in contact with each other as described above, the guidewire GW (in FIG. 6) is held between the guidewire engagement surface 53 and the inner wall surface 264 of the groove 26.

As shown in FIG. 1, the holder 5 is disposed at the distal end of the sheath 2. In this exemplary embodiment, the holder 5 is a three-dimensional hook connected to the tip of the operation wire 3, having a substantially cylindrical outer shape. The hook 5 includes a slit 56 that is formed along the longitudinal axis L direction. As shown in FIG. 2, the hook 5 further includes a proximal end portion 503 having a proximal end surface 505 that abuts on a distal end surface 27 of the sheath 2, and a guidewire engaging surface 53 (in FIG. 1) that is farther than the distal end of the groove 26. As will be described later, the guidewire GW is to be held between the guidewire engagement surface 53 and an inner wall surface 264 of the groove 26, and the hook 5 is configured to be switchable between holding the guidewire GW and releasing the guidewire GW.

Further referring to FIG. 1, the hook 5 also includes a protrusion 58 that is formed in a region where a wire fixing portion 54 (in FIG. 3) is provided. The protrusion 58 includes a contact surface 581 that can contact a side surface of the sheath 2 when the hook 5 is retracted. The contact surface 581 is formed continuously from the inner wall surface 561 of the slit 56, but the contact surface 581 may be provided separately from the slit 56. The protrusion 58 may be provided at a position different from the wire fixing portion 54.

Figure 8:
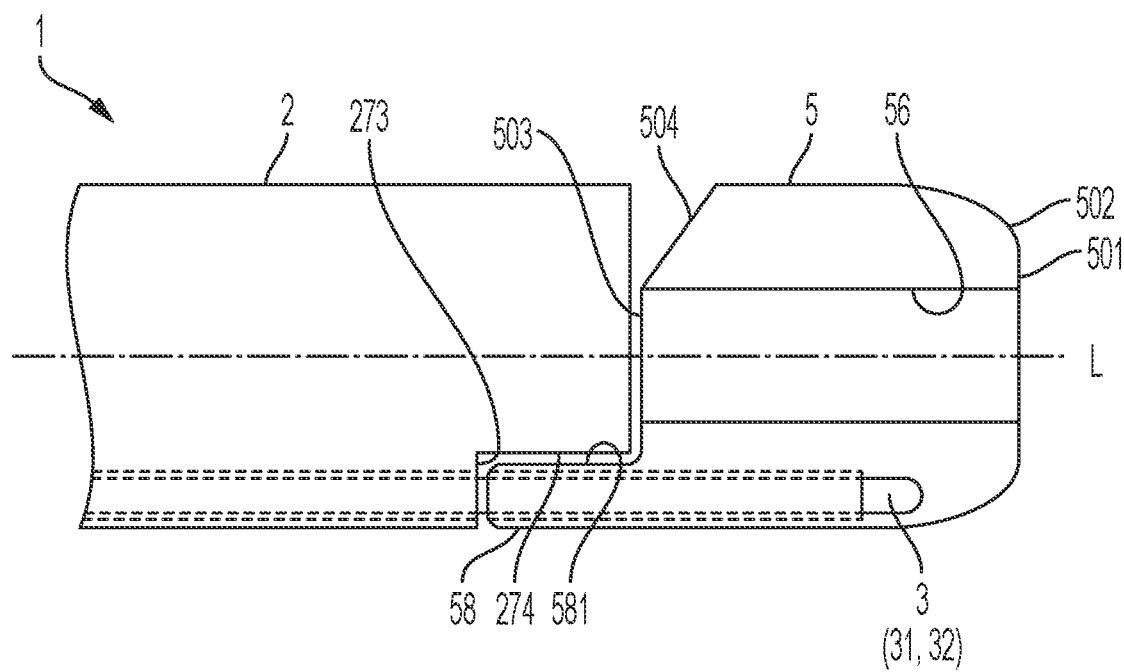
FIG. 8 is a top view showing a modified example of the guidewire holding device according to the exemplary embodiment.

As shown in FIG. 2, the hook 5 further include a tip portion 501 having an curved surface 502 that is formed on an outer peripheral portion of the tip portion 501. Thus, the hook 5 can be smoothly advanced and retracted. In addition, as shown FIG. 8, besides that the tip end portion 501 of the hook is provided with the curved surface 502, the base end portion 503 may be provided with an inclined surface 504. The base end portion 503 of the hook 5 may also be formed as an curved surface. Further, any shape, which is suitable for the hook 5 to be smoothly advanced and retracted, can be used to form the outer peripheral portions of the hook 5.

Figure 5:
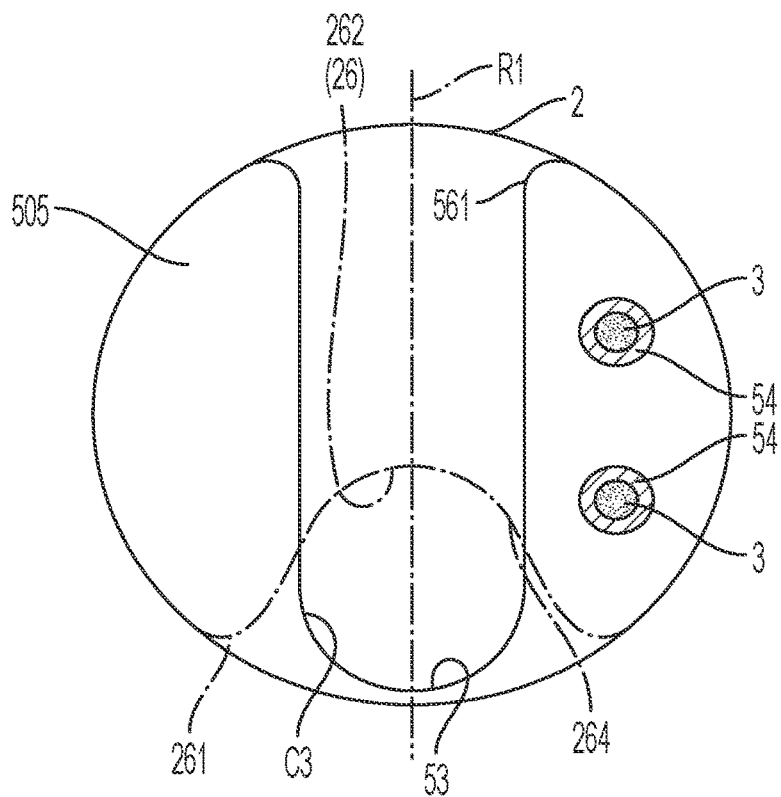
FIG. 5 is a sectional view taken along the line V-V in FIG. 3.

The slit 56 is U-shaped groove. As shown in FIG. 5, the slit 56 is opened on a first diameter line R1 on the outer peripheral surface of the hook 5 and is recessed in the radial direction. The slit 56 is formed to extend over the entire length in the longitudinal axis L direction of the hook 5. In the example shown in FIGS. 1 and 5, a bottom surface of the slit 56 is the guidewire engagement surface 53.

Figure 6:
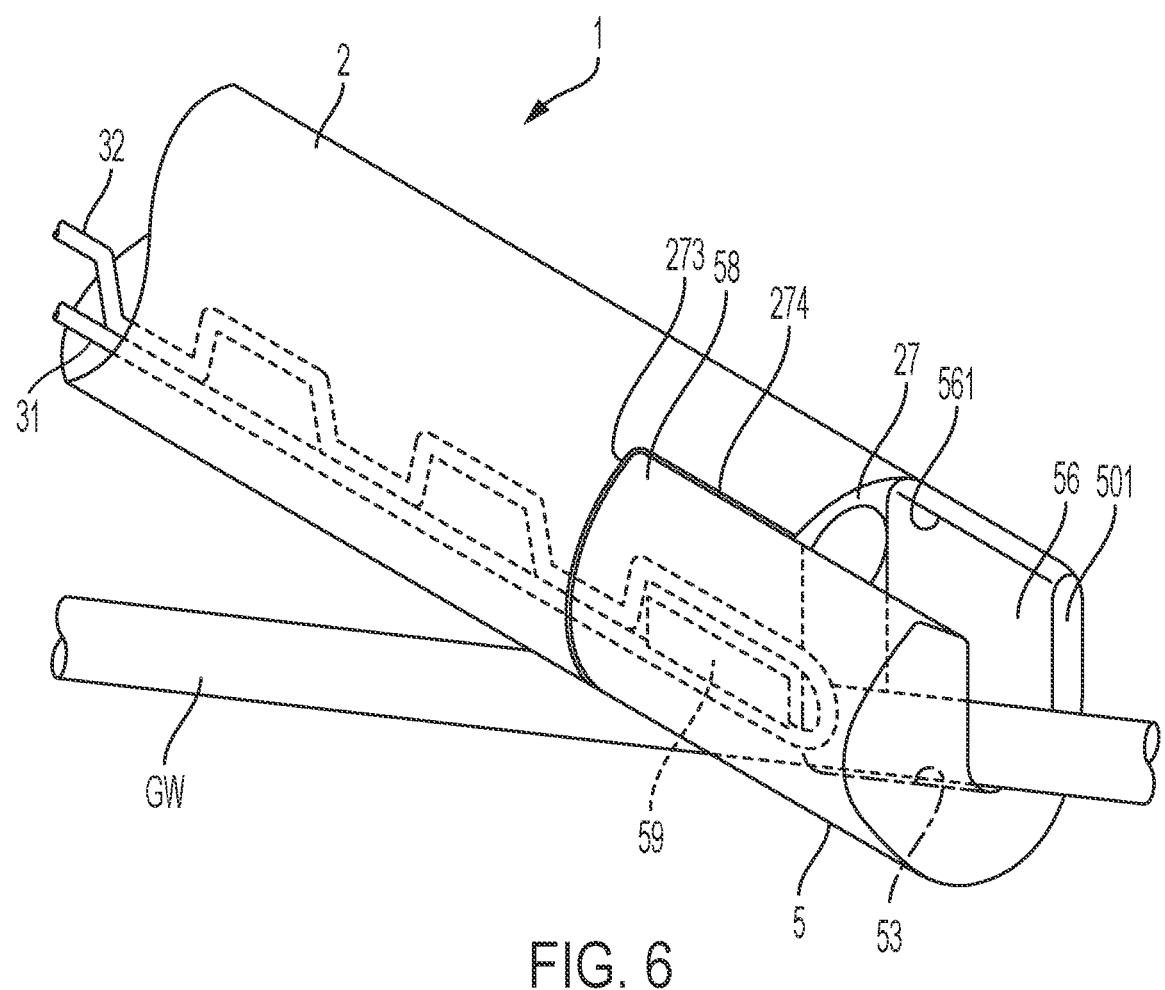
FIG. 6 is a schematic diagram showing, in partial transparent view, a mode of using the guidewire holding device according to an exemplary embodiment.

Referring to FIGS. 5 and 6, the slit 56 is opened in the direction opposite to the opening of the groove 26 of the sheath 2. When viewed from the longitudinal axis direction (when viewed from the front along the longitudinal axis), the guidewire engagement surface 53 of the slit 56 preferably intersects with the tip edge (ridge line) 261 of the curved shape of the groove 26 to form a closed region C3. On the other hand, as shown in FIG. 3, in the direction of the longitudinal axis L, a bottom portion 262 of the groove 26 and the guidewire engagement surface 53 do not face each other, and the slit 56 is located on the tip side of the tip edge 261 of the groove 26.

As shown in FIGS. 3 and 6, the guidewire engagement surface 53 is inclined so as to approach an extension line of the longitudinal axis L of the sheath 2 from the proximal end of the hook 5 toward the distal end. As shown in FIG. 5, the radial position of the guidewire engagement surface 53 at the proximal end portion 503 of the hook 5 is located radially outside the position of the bottom portion 262 of the groove 26. The closed region C3 may be formed as a region that is closed by at least the proximal end portion of the hook 5 and the distal end edge 261 of the groove 26 when viewed in the longitudinal axis direction. Therefore, the guidewire GW captured in the closed region C3 can smoothly move back and forth in the closed region C3. As a result, when inserting the distal end portion of the guidewire holding device 1 into the duodenum, the sheath 2 can be easily advanced along the guidewire GW. The groove 26 of the sheath 2 is formed on the extension of the inclination of the guidewire engagement surface 53.

The hook 5 is a member made of resin in this exemplary embodiment. The hook 5 may be any material that has sufficient strength when it is formed into a small shape in consideration of insertability of the duodenal papilla. The hook 5 may be made of metal. Further, the hook 5 may be formed by combining metal and resin. For example, if the inner wall surface 561 of the slit 56 is made of resin, the guidewire GW can be slid smoothly.

As shown in FIG. 3, the wire fixing portion 54, into which the operation wire 3 is inserted and fixed, is provided between the slit 56 and the outer peripheral surface of the hook 5. The wire fixing portion 54 is provided with a U-shaped communication hole in which two lumens extending in parallel to the longitudinal axis L communicate with each other at the tip portion, and the operation wire 3 is inserted into the communication hole and fixed by, for example, an adhesive. The method of fixing the operation wire 3 in the wire fixing portion 54 is not limited to the adhesive. The operation wire 3 may be fixed in the wire fixing portion 54 by fitting, crimping, or the like.

Figure 4:
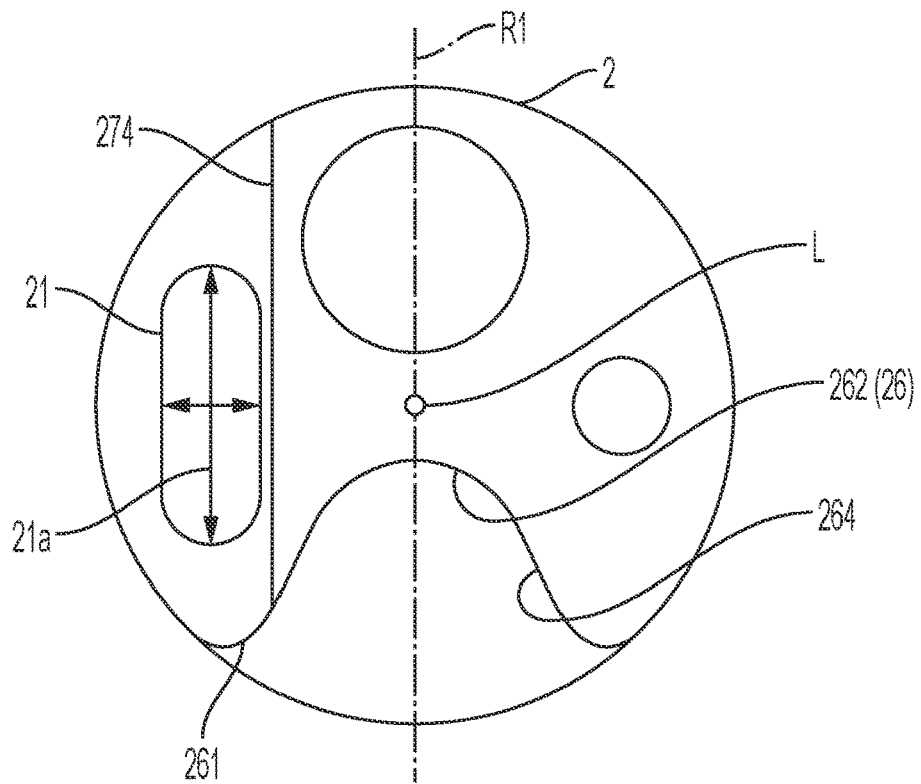
FIG. 4 is a front view of the sheath of an exemplary embodiment.

The operation wire 3, as shown in FIG. 1, may include first and second portions 31 and 32 that extend in the longitudinal axis L direction. The first wire portion 31 may extend linearly in parallel with the longitudinal axis L, and the second wire portion 32 may be bent at a plurality of places so as to be uneven in the vertical direction in side view. The proximal end of the first wire portion 31 is fixed to the operation slider 42 of the operation unit 4. The proximal end of the second wire portion 32 is arranged inside the lumen 21. That is, the base end of the second wire portion 32 is arranged inside the lumen 21 without being connected to the operation portion 4. As shown in FIG. 2, the first wire portion 31 and the second wire portion 32 extend so as to overlap the longitudinal axis L in a top view. The first wire portion 31 and the second wire portion 32 are inserted in the lumen 21 of the sheath 2 so as to be able to move forward and backward. As shown in FIG. 4, the lumen 21 has an oblong shape at least in the tip opening portion formed at the step portion 273. The lumen 21 is formed such that the long side 21a of the lumen 21 is parallel to the side surface 274. With this configuration, the lumen 21 and the side surface 274 of the step portion 273 function as a restriction portion, and the two operation wires 31 and 32 and the contact surface 581 serve as a restricted portion. As a result, the rotation around the axis is more stable than the configuration in which the operation wire 3 is regulated only by the lumen 21. Also, as the second wire portion 32 moves in the vertical direction, the concave and convex shape of the second wire portion 32 is stably maintained, thereby effectively preventing the rotation of the hook 5 around the axis. That is, when a force is applied to the hook 5 in the direction of pulling the hook 5 to the proximal side, for example, when the operation slider 42 is pulled, it is difficult for an external force to be applied to the second wire portion 32, and deformation of the vertical uneven shape can be prevented.

The guidewire engagement surface 53 of the hook 5 and the inner wall surface 264 of the groove 26 of the sheath 2 are arranged so that the guidewire GW can be held between the hook 5 and the groove 26 so as to be able to move back and forth.

As shown in FIG. 6, since the guidewire engagement surface 53 of the slit 56 is inclined so that the distal end portion of the slit 56 is located in the vicinity of the central axis of the sheath 2, the guidewire GW is not attached to the sheath at the distal end portion 501 of the hook 5. As a result, when inserting the distal end portion of the guidewire holding device 1 into the duodenum, the sheath 2 can be easily advanced along the guidewire GW. Also, as in FIG. 6, the hook 5 is provided with an X-ray marker 59 that can be visually recognized in an X-ray image. In this exemplary embodiment, the X-ray marker 59 is arranged in a folded-back portion of the distal end portion of the operation wire 3 and embedded in the hook 5. The folded-back portion of the distal end portion of the operation wire 3 may be configured to protrude from the distal end of the hook 5.

Figure 7A:
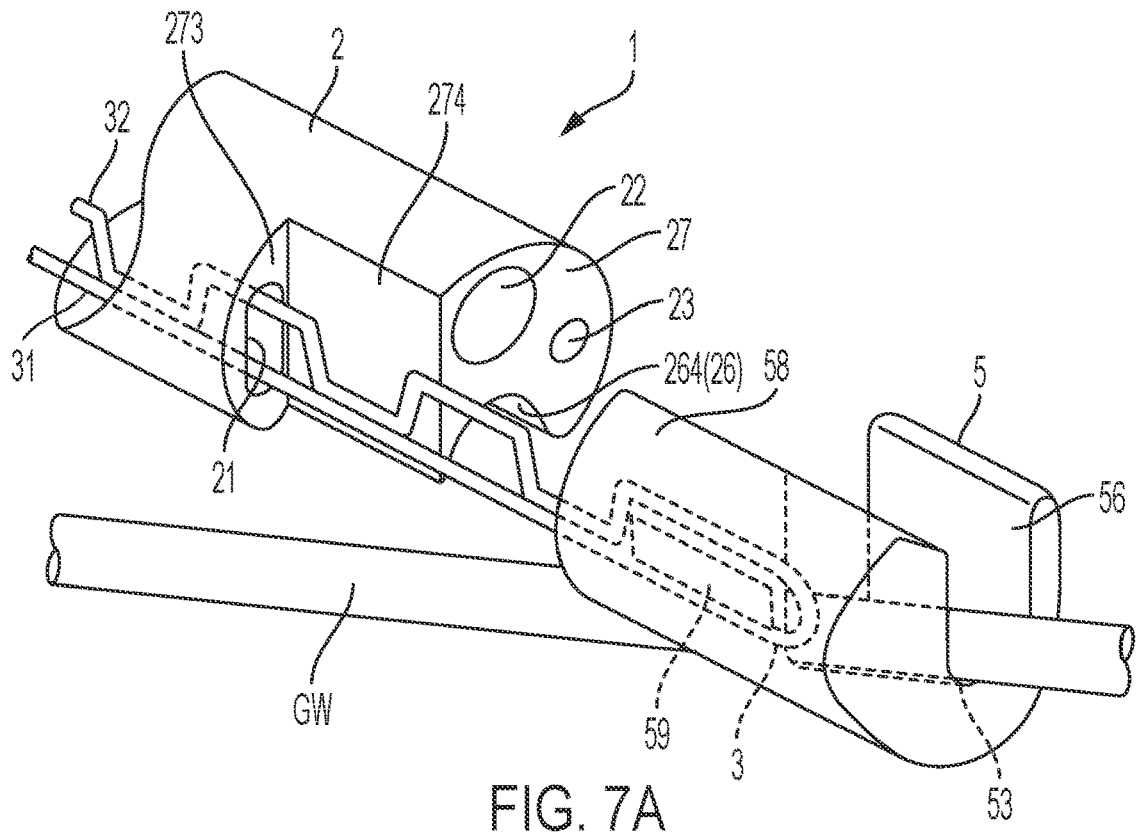
FIG. 7(A) is a schematic diagram showing, in partial transparent view, another mode of using the guidewire holding device according to an exemplary embodiment.

FIG. 7(A) shows a mode in which the hook 5 is advanced out of the sheath 2. While keeping the hook in this status, the guidewire GW can be easily caught into the slit 56 of the hook 5 and also can be positioned corresponding to the groove 26 of the sheath 2. Then, when the guidewire GW is kept inside the slit 56, the hook 5 is retracted toward the sheath 2, thereby holding the guidewire GW between the slit 56 of the hook 5 and the groove 26 of the sheath 2.

Figure 7B:
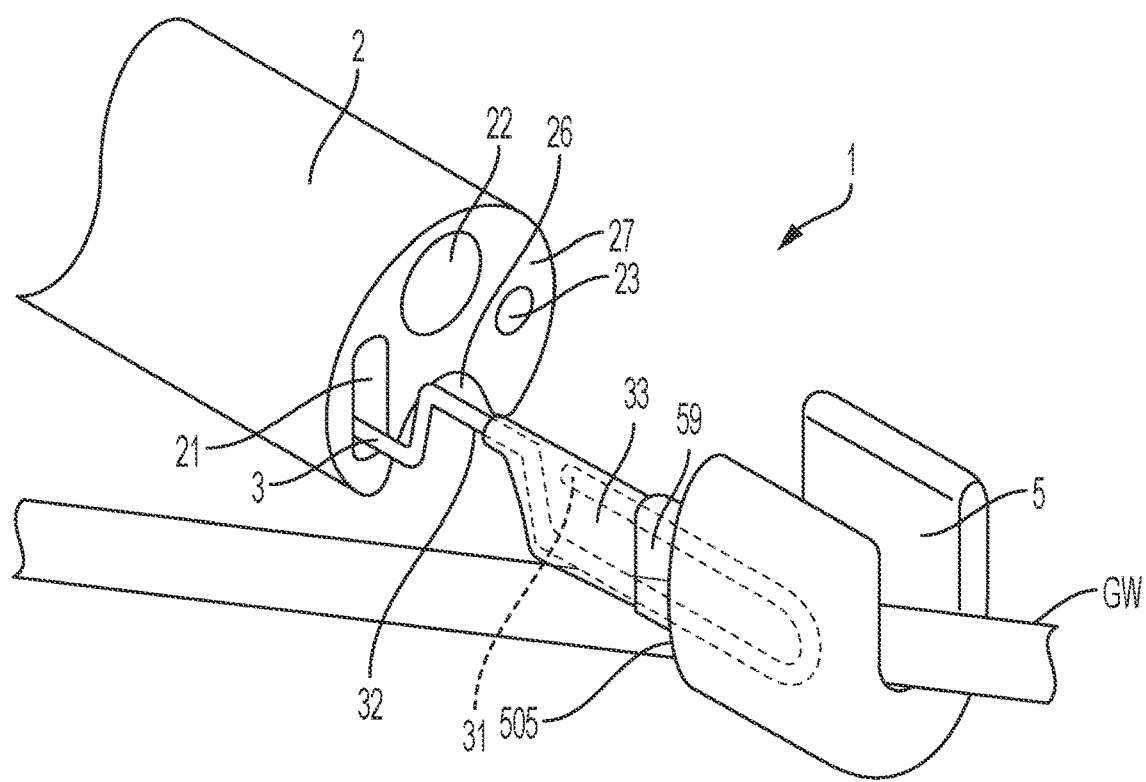
FIG. 7(B) is a perspective view showing the same mode of using a different guidewire holding device according to another exemplary embodiment.

FIG. 7(B) shows the same mode of FIG. 7(A), but a different guidewire holding device from the one shown in FIG. 7(A). As shown in FIG. 1 through FIG. 7(A), the exemplary embodiment shows that the sheath 2 includes a concave portion (which is formed by the step portion 273 and the side surface 274) that can engages with a convex portion (which is formed by the contact surface 581) of hook 5. However, the invention is not limited to this configuration. As an example, FIG. 7(B) shows that the sheath 2 may include a flat distal end surface 27 without the concave shape of FIG. 7(A), and the hook 5 may include a flat base end face 505 without the convex contact surface 581 of FIG. 7(A). Also, as shown in FIG. 7(B), the X-ray marker 59 is arranged outside the hook 5 to cover at least part of the folded-back portion of the distal end portion of the operation wire 3 and a covering tube 33 is arranged to cover at least part of the distal end of the operation wire 3 that is exposed between the sheath 2 and the hook 5. By this configuration of FIG. 7(B), when the hook 5 is retracted to the sheath 2, the covering tube 33 and the X-ray marker 59 are accommodated inside the lumen 21 of the sheath 2. The lumen 22 may be used to deliver the treatment tool 24. The lumen 23 may be used as a liquid delivering lumen, or may be used to deliver additional treatment tool.

The X-ray marker 59 is made of an X-ray opaque material, and serves to determine the position of the distal end of the hook 5 under X-ray fluoroscopy.

In this exemplary embodiment, during an EUS-RV procedure, the treatment device 24 is configured to be switchable between a first configuration or status and a second configuration or status. FIG. 1 shows that the treatment device 24 is in the first configuration when the treatment device 24 is contained inside the lumen 22 of the sheath 2. After the guidewire holding device 1 is inserted into the bile duct along the guidewire GW, the treatment device 24 (in FIG. 17(A)-17(E)) is protruded from the distal end of the sheath 2, thereby switching into the second configuration. Under the second configuration, the treatment device 24 performs the intended ERCP procedure.

The treatment device 24 may be any endoscopic treatment tool that is able to be stored inside the sheath 2 in the first configuration or be mounted on the sheath 2, and is capable of performing an ERCP procedure in the second configuration. The examples of the treatment device 24 will be described later based on FIG. 17(A)-17(E).

Figure 9:
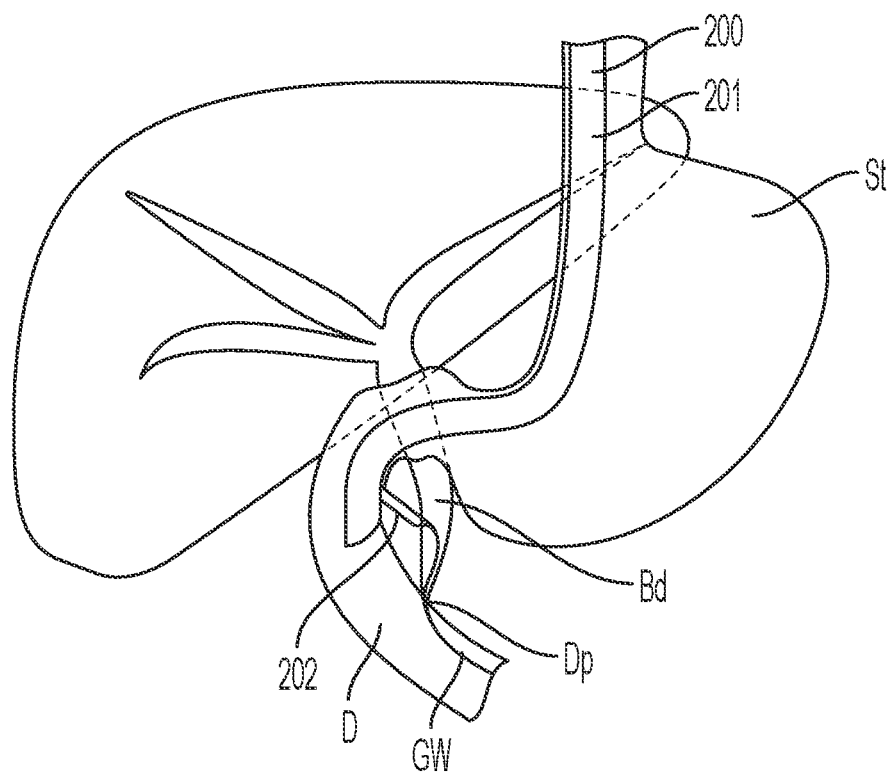
FIG. 9 is a diagram illustrating a method of introducing the guidewire holding device into a hollow organ according to an exemplary embodiment.
Figure 10:
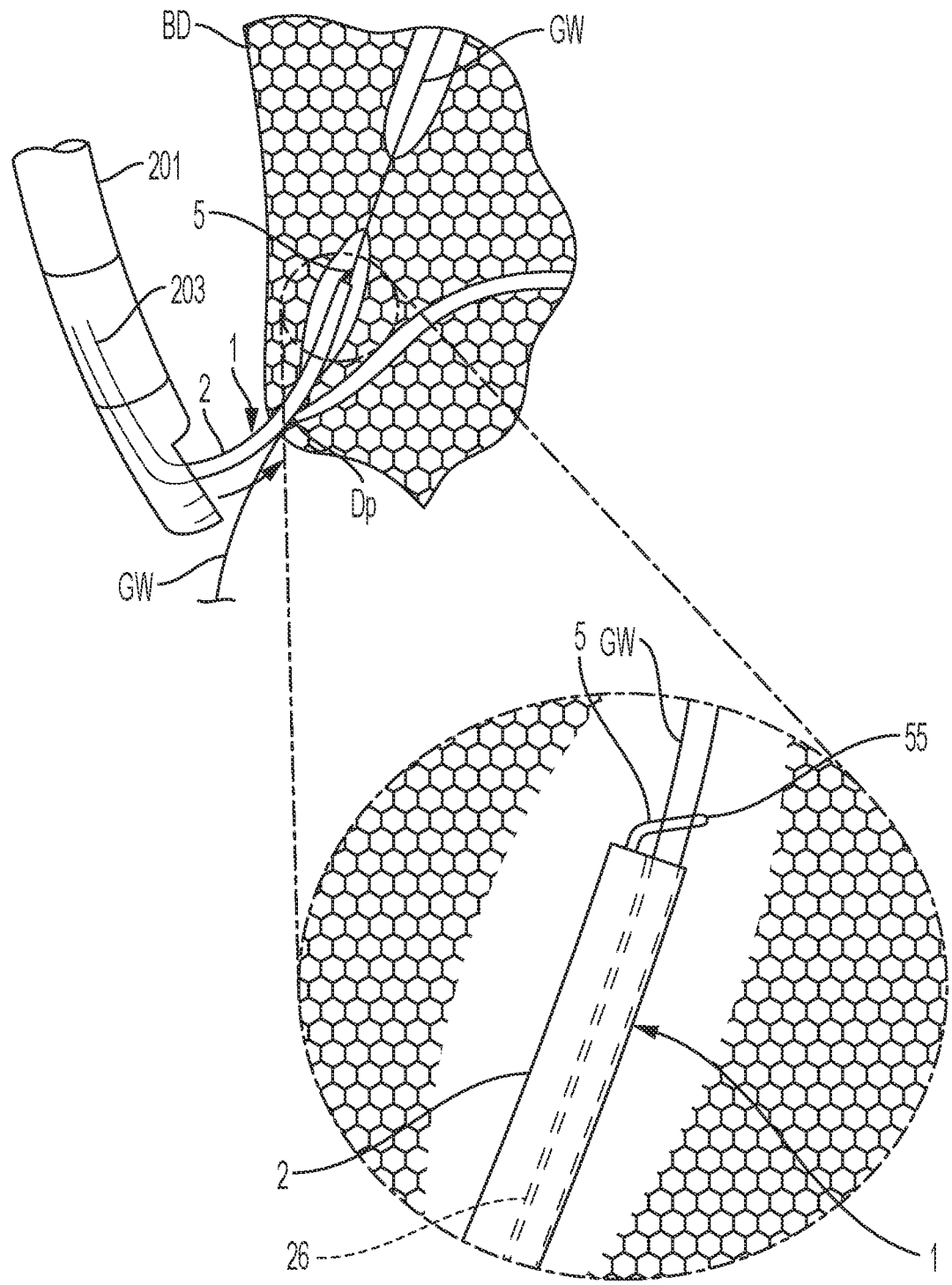
FIG. 10 is a diagram illustrating a method of showing an example of performing a procedure by a rendezvous method using the guidewire holding device according to the exemplary embodiment.

Next, a method of introducing the guidewire holding device 1 into the luminal organ, for example, the bile duct by the rendezvous method will be described as an example. FIGS. 9 and 10 are schematic views showing the method of inserting the guidewire holding device 1 and indwelling a treatment tool to perform an ERCP procedure.

First, the guidewire GW is placed in the duodenum D. Specifically, as shown in FIG. 9, an endoscope insertion portion 201 of an ultrasonic endoscope 200 is inserted from the patient's mouth to the stomach St or the duodenum D. An access needle 202, which is inserted into the endoscope insertion portion 201 and protrudes from the tip of the endoscope insertion portion 201, is punctured into the bile duct Bd. After that, the guidewire GW is inserted into the endoscope insertion portion 201, and then inserted into the bile duct Bd via a lumen of the access needle 202. When the guidewire GW is inserted into the bile duct Bd, the guidewire GW is pushed forward so that the tip of the guidewire GW is projected from the duodenal papilla Dp and inserted into the duodenum D. By advancing the guidewire GW toward the duodenal papilla Dp, the tip of the guidewire GW protruding from the duodenal papilla Dp extends along the lumen of the duodenum D.

Then, the ultrasonic endoscope 200 is removed with the guidewire GW left inside the body of a patient, and the tip of the guidewire GW is left in the duodenum D. At this time, the proximal end side of the guidewire GW is outside the body of a patient.

Next, as shown in FIG. 10, the endoscope insertion portion 201 of a duodenoscope (not shown) is inserted from the patient's mouth to the duodenum D. Then, the guidewire holding device 1 is inserted into the endoscope insertion portion 201, and the distal end portion of the sheath 2 is projected from the distal end of the endoscope insertion portion 201. Then, the operation slider 42 is advanced to the distal end side, so that the operation wire 3 is advanced with respect to the sheath 2 thereby advancing the hook 5 to the advanced position with respect to the sheath 2. The sheath 2 is guided in a direction in which the hook 5 is hooked on the guidewire GW.

Next, the operator retracts the operation slider 42 to the proximal end side, so that the operation wire 3 is retracted with respect to the sheath 2, thereby placing the hook 5 in the retracted position. By retracting the hook 5 to the retracted position, the guidewire GW can be brought close to the tip edge 261 of the groove 26. In the retracted position, as described above, the guidewire GW is captured and held in the closed region C3 formed between the groove 26 of the sheath 2 and the slit 56 of the hook 5. The guidewire GW captured in the closed region C3 can smoothly move back and forth in the closed region C3.

Next, with the guidewire GW held in the closed region C3 between the slit 56 and the groove 26, the distal end portion of the sheath 2 is attached to the duodenal papilla Dp along the guidewire GW while pressing the inner wall surface of the groove 26 against the guidewire GW. The operator pushes the operating portion 4 to insert the distal end portion of the sheath 2 into the duodenal papilla Dp as shown in FIG. 9. As the guidewire GW has already passed through the bile duct Bd and extended to the duodenum D via the duodenal papilla Dp, when the guidewire holding device 1 is pushed in, the sheath 2 advances along the guidewire GW and reaches the inside of the bile duct Bd.

At this time, the treatment device 24 is in a first status in which it is contained inside the sheath 2 of the guidewire holding device 1. After the insertion of the guidewire GW into the bile duct Bd is completed, the treatment device 24 is switched into a second status, in which it is protruded from the distal end of the guidewire holding device 1, which has been inserted into the duodenum along the guidewire GW. Once the treatment device 24 is protruded into the bile duct, the intended ERCP procedure is performed.

After the intended ERCP procedure is completed, the holding of the guidewire GW is released. The treatment device 24 is switched from the second status back into the first status by retracting into the guidewire holding device 1. After that, the guidewire holding device 1 is removed from the endoscope insertion portion 201.

Figure 11:
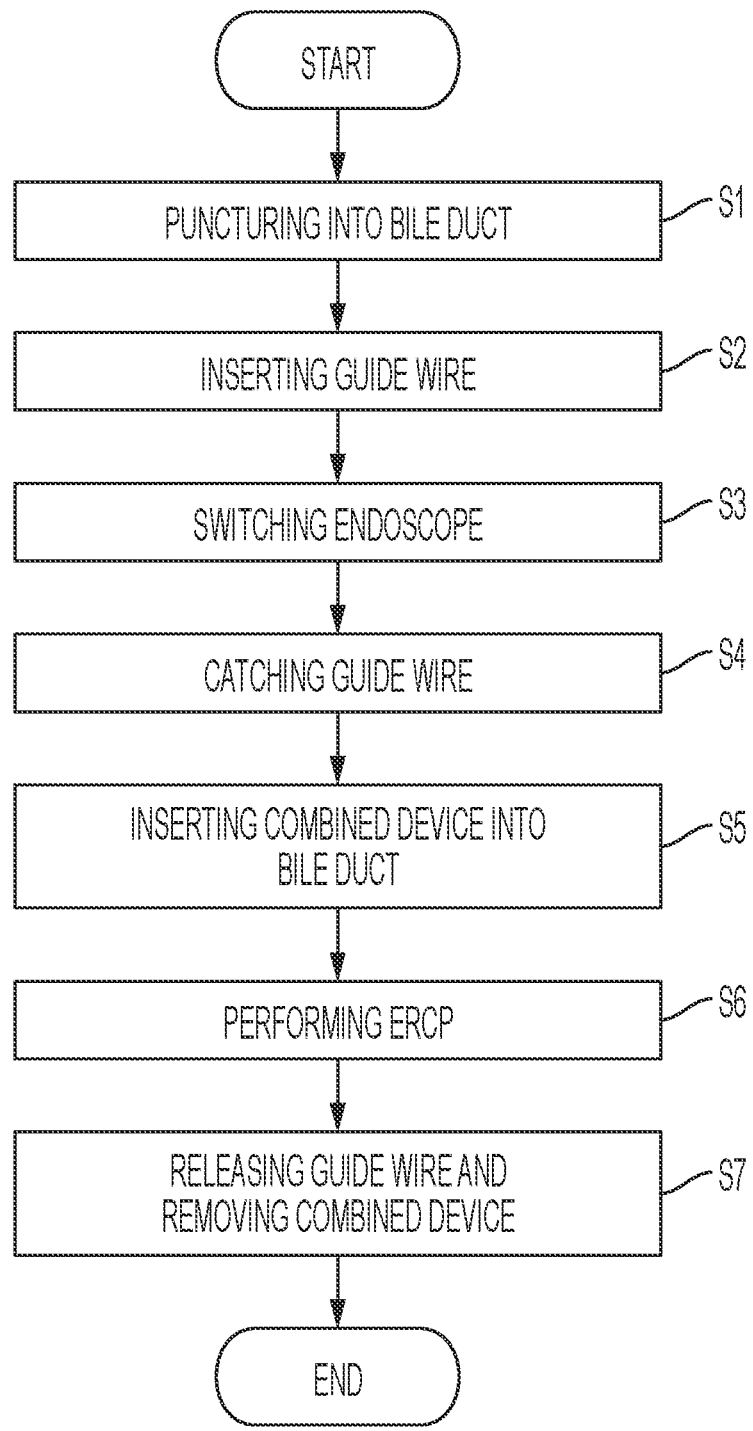
FIG. 11 is a flowchart illustrating general steps of a method of introducing the guidewire holding device into a hollow organ according to an exemplary embodiment.

FIG. 11 is a flowchart showing the method for inserting the guidewire holding device 1 into the bile duct to indwell the treatment device 24 to perform the ERCP procedure according to this exemplary embodiment.

As shown in FIG. 11, the above described method of inserting the guidewire holding device to perform the intended treatment may be divided into the following steps.

At Step S1, the bile duct is punctured by a puncturing needle. Specifically, an access needle 202, which is inserted into the endoscope insertion portion 201 and protrudes from the tip of the endoscope insertion portion 201, is punctured into the bile duct Bd.

At Step S2, the guidewire GW is inserted into the duodenum D. Specifically, the guidewire GW is inserted into the endoscope insertion portion 201, and then inserted into the bile duct Bd via the access needle 202. When the guidewire GW is inserted into the bile duct Bd, the operator pushes the guidewire GW forward so that the tip of the guidewire GW is projected from the duodenal papilla Dp and enters into the duodenum D. By advancing the guidewire GW toward the duodenal papilla Dp, the tip of the guidewire GW protruding from the duodenal papilla Dp extends along the lumen of the duodenum D.

At Step S3, an endoscope switching process is performed. Specifically, the ultrasonic endoscope 200 is removed with the guidewire GW left inside the body of a patient, and the tip of the guidewire GW is left in the duodenum D. The endoscope insertion portion 201 of a duodenoscope is inserted from the patient's mouth to the duodenum D.

At Step S4, a guidewire catching process is performed. Specifically, the guidewire holding device 1 is inserted into the endoscope insertion portion 201, and the distal end portion of the sheath 2 is projected from the distal end of the endoscope insertion portion 201. At this time, the guidewire holding device 1, which is located at the distal end portion of the sheath 2, is guided in a direction in which the hook 5 of the guidewire holding device 1 can be easily hooked on the guidewire GW and also the guidewire GW can be easily pushed into the groove 26. As a result, the guidewire GW is captured and held within the closed region C formed by the slit 56 of the hook 5 and the groove 26. The guidewire GW can smoothly move back and forth in the closed region C. Alternatively, at Step S4, the guidewire GW may be inserted into the patient's body from an additional lumen of the sheath 2. In this situation, the guidewire holding device 1 can catch the guidewire GW without pushing the guidewire GW into the groove 26 of the sheath 2.

At Step S5, a cannulation process is performed. Specifically, with the guidewire GW held between the slit 56 of the hook 5 and the groove 26, the distal end portion of the sheath 2 is attached to the duodenal papilla Dp along the guidewire GW while pressing the inner wall surface 264 of the groove 26 against the guidewire GW. The operator pushes the operating portion 4 to insert the distal end portion of the sheath 2 into the duodenal papilla Dp as shown in FIG. 10. As the guidewire GW has already passed through the bile duct Bd and extended to the duodenum D via the duodenal papilla Dp, when the guidewire holding device 1 is pushed in, the sheath 2 advances along the guidewire GW and reaches the inside of the bile duct Bd. At this time, the treatment device 24 is in the first status in which it is contained inside the sheath 2 or is mounted on the sheath 2.

At Step S6, the ERCP procedure is performed. Specifically, after the insertion of the guidewire GW into the bile duct Bd is completed, the treatment device 24 is switched into the second status, in which it is protruded from the guidewire holding device 1. As described above, before the ERCP is performed, the treatment device 24 is in the first status in which the treatment device 24 is contained inside the sheath 2. Once the treatment device 24 is switched into the second status in which the treatment device 24 is protruded from the guidewire holding device 1 disposed at the distal end of the sheath 2, the intended ERCP procedure is performed in the target organ.

At Step S7, after the intended ERCP procedure is completed, the holding of the guidewire GW is released. The treatment device 24 is retracted into the sheath 2 of the guidewire holding device 1. Thus, the treatment device 24 is switched from the second status into the first status. Then, the guidewire holding device 1 having the treatment device 24 inside thereof is removed out to the duodenum, and the guidewire GW is removed out of the body of a patient.

Examples of the treatment device 24 of the guidewire holding device 1 will be described below based on FIGS. 12-20(D). Some of these drawings show exemplary embodiments that the sheath does not include a groove. However, even in these exemplary embodiments, the sheath may also include the groove as described above.

Figure 12:
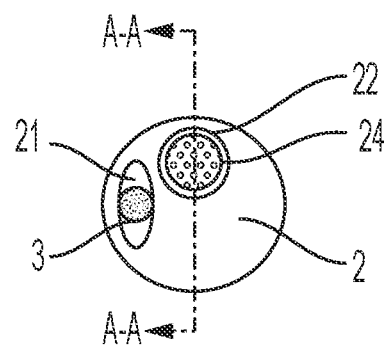
FIG. 12 is a front view of a sheath schematically showing a guidewire holding device including a treatment device contained inside the sheath.
Figure 13:
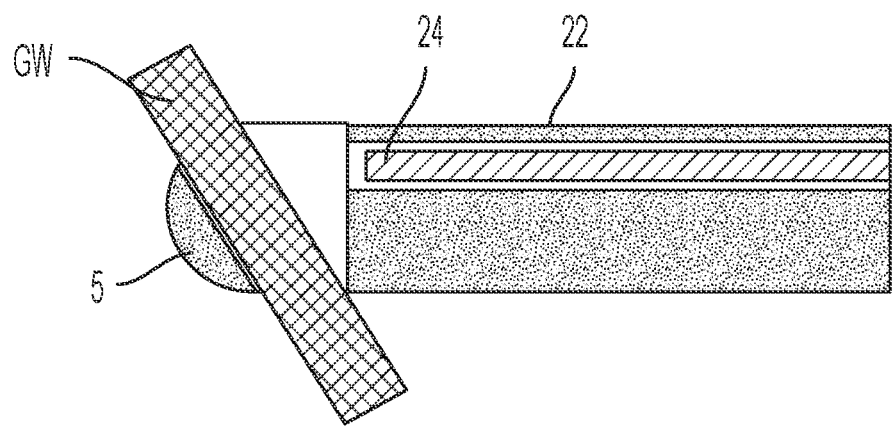
FIG. 13 is a cross-sectional view of line A-A of FIG. 12 schematically showing the treatment device in a first configuration in which the treatment is contained inside the sheath.

FIG. 12 is a front view of the sheath 2 schematically showing the guidewire holding device 1 in which the treatment device 24 is contained inside the sheath 2. FIG. 13 is a cross-sectional view of line A-A of FIG. 12 schematically showing the first configuration of the treatment device 24.

As shown in FIGS. 12 and 13, in this exemplary embodiment, the treatment device 24 is a basket wire for collecting the stones inside the bile duct. In the first configuration, the basket wire is kept inside a lumen (lumen 22 in FIG. 1) of a sheath, and thus a basket disposed at a distal end of the basket wire is not opened.

Figure 14A:
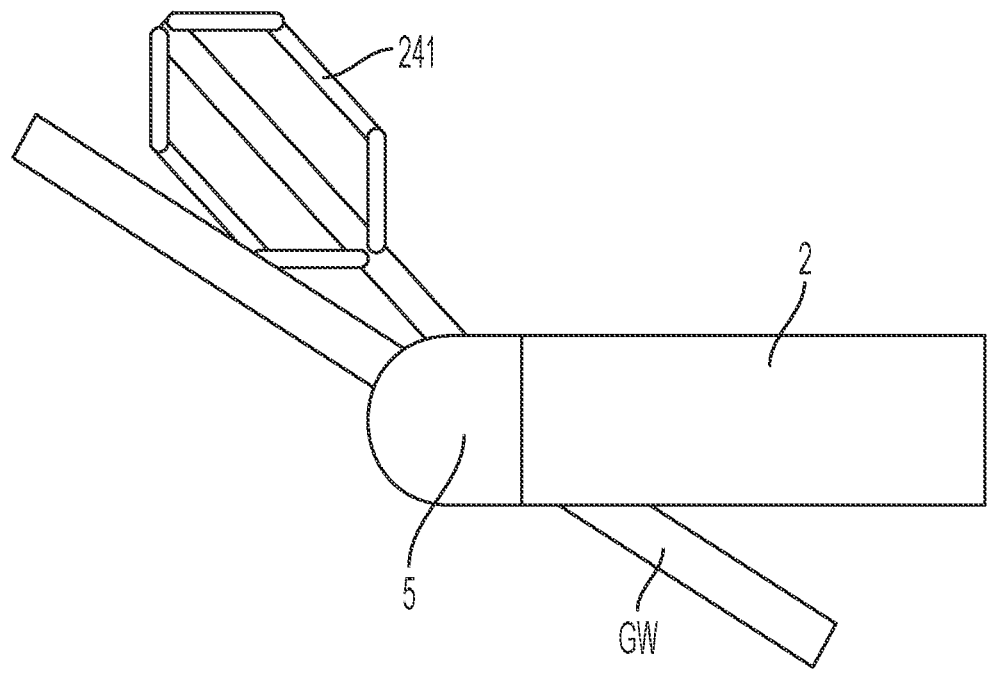
FIG. 14(A) is a perspective side view of a guidewire holding device in which a treatment device is protruded from a sheath according to an exemplary embodiment.
Figure 14B:
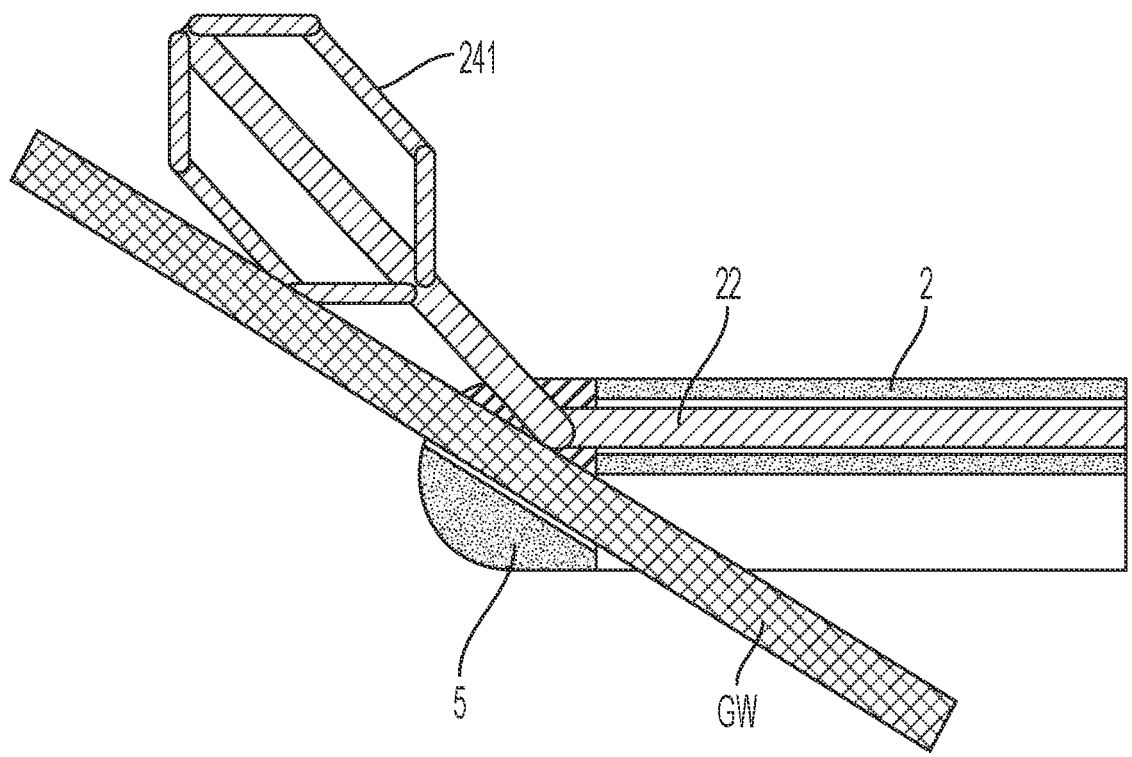
FIG. 14(B) is a cross-sectional side view of the guidewire holding device in which the treatment device is protruded from the sheath according to an exemplary embodiment.
Figure 14C:
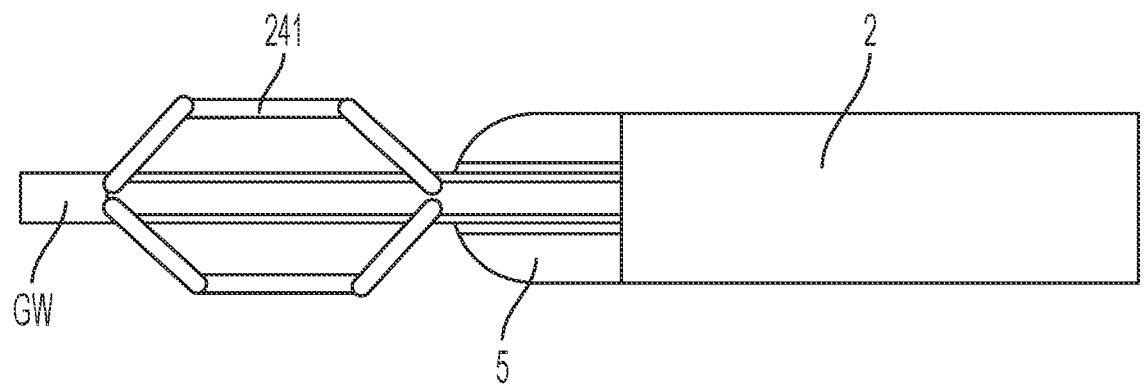
FIG. 14(C) is a top view of the guidewire holding device in which the treatment device is protruded from the sheath according to an exemplary embodiment.
Figure 14D:
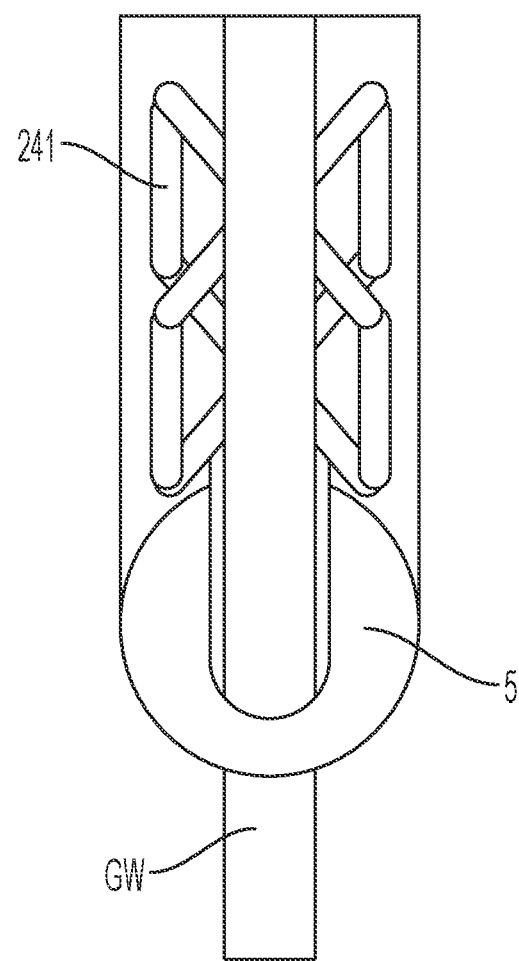
FIG. 14(D) is a front view of the guidewire holding device in which the treatment device is protruded from the sheath according to an exemplary embodiment.

FIG. 14(A) is a perspective side view of the guidewire holding device 1 in which the treatment device 24 is protruded from the sheath 2, FIG. 14(B) is a cross-sectional side view of the guidewire holding device 1 in which the treatment device 24 is protruded from the sheath 2, FIG. 14(C) is a top view of the guidewire holding device 1 in which the treatment device 24 is protruded from the sheath 2, and FIG. 14(D) is a front view of the guidewire holding device 1 in which the treatment device 24 is protruded from the sheath 2. As shown in FIG. 14(A)-14(D), the treatment device 24 is a basket wire 241. The basket wire 241 inside the lumen 21 is advanced in parallel with the sheath 2 in the longitudinal axis L direction. When the basket of the basket wire is protrude out of the sheath 2, the basket is opened and switched into the second configuration. Also the basket wire 241 slightly changes its advancing direction when the basket wire 241 contacts with the guidewire GW. The basket of the basket wire 241 is moved to the target organ along with the guidewire GW.

Figures 15A, 15B:
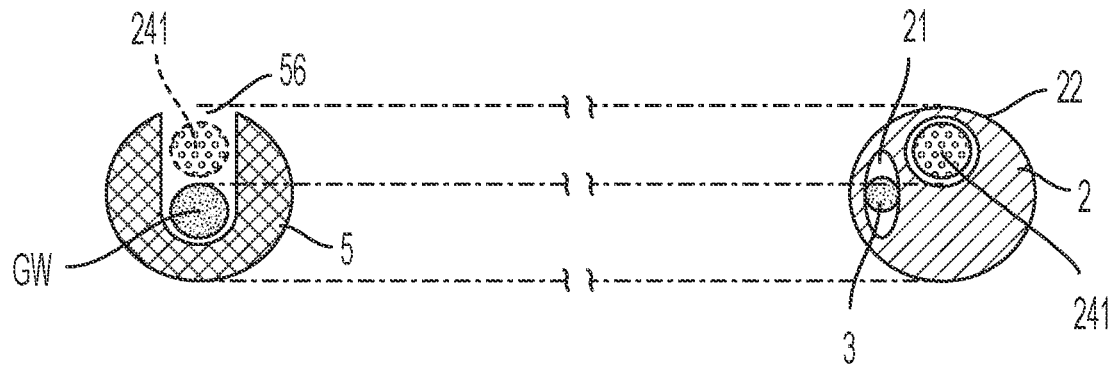
FIG. 15(A) is a front view of a holder schematically showing a treatment device in a second configuration in which it is protruded from a sheath 2, and FIG. 15(B) a front view of a sheath schematically showing the treatment device in the second configuration.

FIG. 15(A) a front view of the hook schematically showing the second configuration of the basket wire in which it is protruded from the sheath. FIG. 15(B) a front view of the sheath schematically showing the same situation. As shown in FIG. 15(A), the basket wire is positioned above the guidewire GW and passes through the slit of the hook. Furthermore, the slit has a width equal to or larger than a diameter of the lumen and a depth equal to or larger than a sum of a diameter of the guidewire and a diameter of the basket wire. In some embodiments, a central axis of the slit substantially coincides with a center of the lumen (as viewed in a radial cross-section).

Figures 16A, 16B:
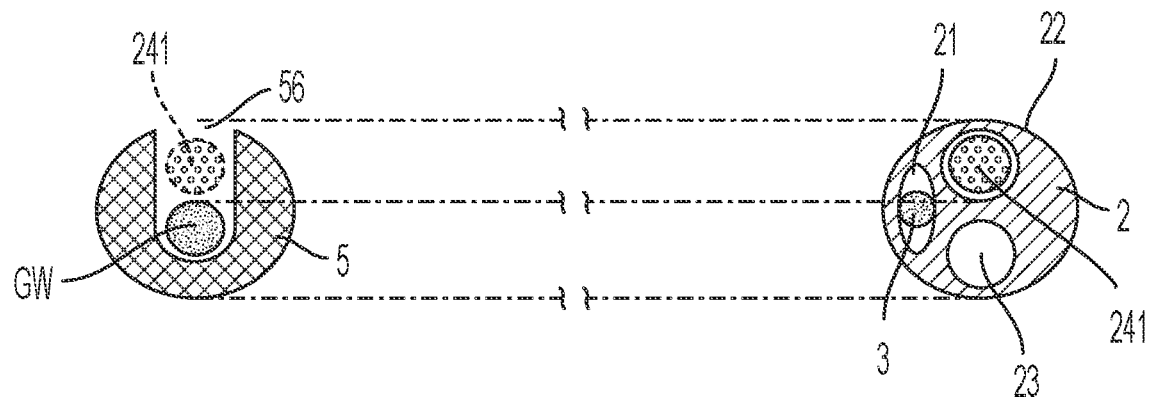
FIG. 16(A) a front view of a holder schematically showing that a treatment device is protruded from a sheath, and FIG. 16(B) a front view of a sheath schematically showing that the treatment device is protruded from the sheath.

FIG. 16(A) a front view of the hook schematically showing that the basket wire is protruded from the sheath which includes additional lumen for a second guidewire. FIG. 16(B) a front view of the sheath schematically showing the second lumen. The additional lumen communicates with the slit of the hook and the slit has a width equal to or larger than a diameter of the additional lumen. However, since the slit is positioned overlapping with the additional lumen in the front view of the hook, the additional lumen is not shown in FIG. 16(A). The second guidewire, which is inserted into the additional lumen after the first guidewire is released from the hook, will be also passed through the slit as shown in FIG. 16(A). By such a configuration, the second guidewire is able to move forward and backward to the hook.

As shown in FIG. 16(B), the sheath may be provided with additional lumen for a second guidewire. The second guidewire can be used to insert and indwell additional treatment device without increase a diameter of the sheath. Alternatively, as described herein, the first guidewire GW may be inserted into the patient's body through the additional lumen, and the second guidewire may be inserted into the patient's body through another different lumen without increase the diameter of the sheath.

The treatment device 24 may be any treatment tool that is configured to be stored inside the sheath 2 or mounted on the sheath 2 in the first configuration before the intended treatment, and to be switched to the second configuration in which it is protruded from the guidewire holding device when the intended treatment starts. The basket wire described above is one example. Other examples of such a treatment tool include, but are not limited to, an electrode knife wire, Diathermic dilator, ablation probe, balloon catheter, cytology brush, biopsy forceps, grasping forceps, thin endoscope, puncture needle, and the like. These examples will be described below according to FIG. 17(A)-17(E).

Figure 17A:
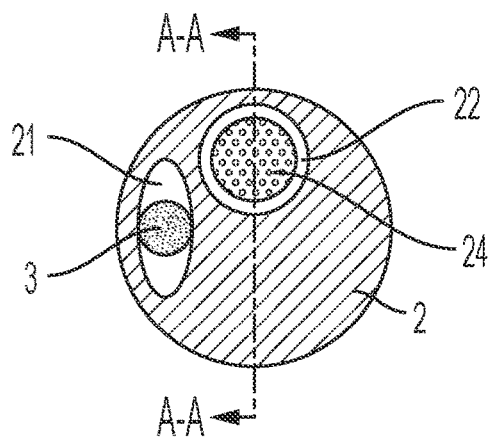
FIG. 17(A)-17(E) show the examples of a treatment device in first and second status/configurations according to the exemplary embodiment.
Figure 17B:
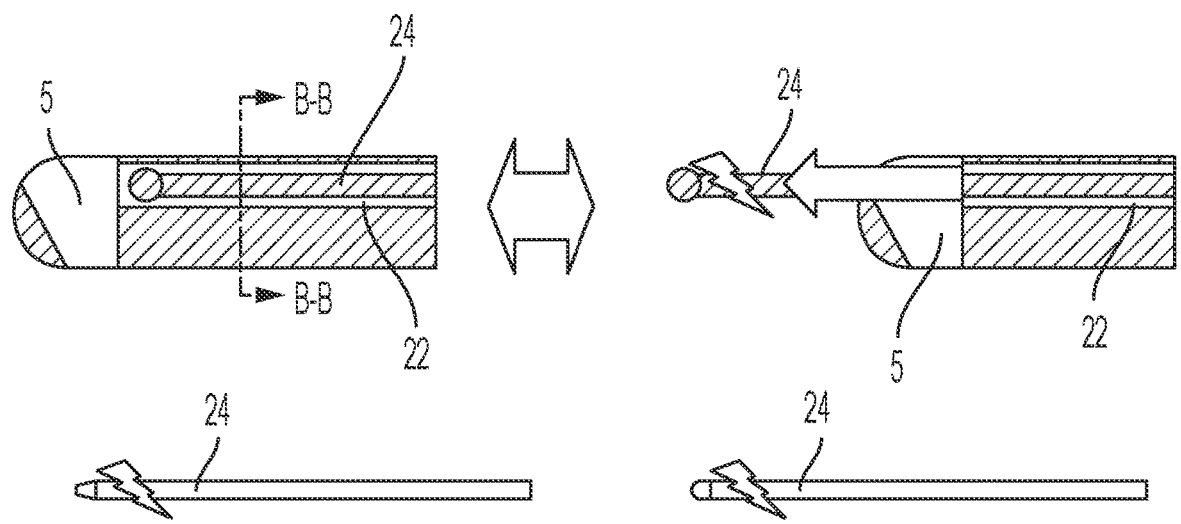

FIG. 17(A)-17(E) show the examples of the treatment device that are applicable in the exemplary embodiment. FIG. 17(A) is a cross-sectional view of line B-B in FIG. 17(B) schematically showing a front view of sheath. FIG. 17(B) shows two cross-sectional views of line A-A in FIG. 17(A) schematically illustrating side views of the guidewire holding device when one example of the treatment device is stored inside the sheath in the first configuration and then is switched into the second configuration in which the one example of the treatment device is protruded from the sheath.

In this example, the treatment device may be an electrode knife wire. The left side view of FIG. 17(B) shows that the electrode knife wire is powered off when it is stored inside the sheath. The right side view of FIG. 17(B) shows that the electrode knife wire is powered on when it is protruded from the sheath so that the electrode knife wire is able to perform the intended ERCP procedure. Also, as shown in 17(B), instead of the electrode knife wire, a Diathermic dilator or an ablation probe may also be used as the treatment device in this example. That is, the Diathermic dilator and the ablation probe can be powered off when they are contained inside the sheath in their first configuration, and be powered on when they are protruded from the sheath in their second configuration.

Figure 17C:
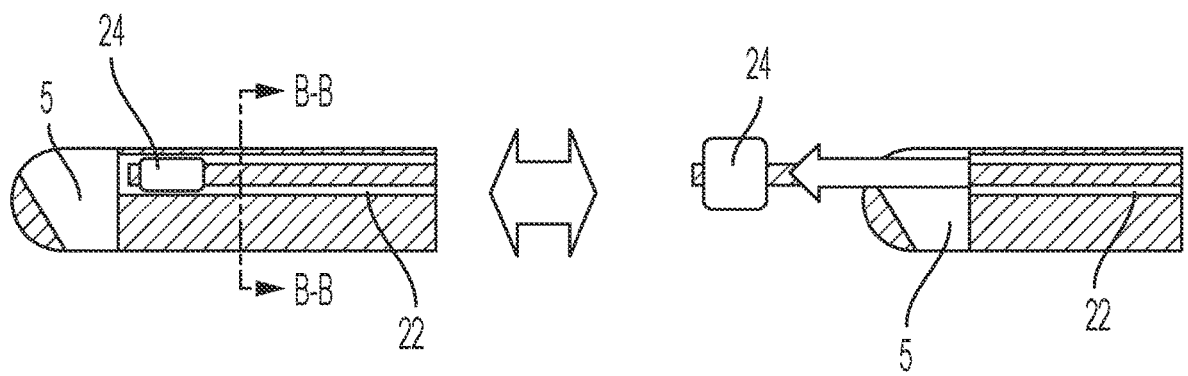

FIG. 17(C) shows two cross-sectional views of line A-A in FIG. 17(A) schematically illustrating side views of the guidewire holding device when another example of the treatment device is stored inside the sheath in the first configuration and then is switched into the second configuration in which the another example of the treatment device is protruded from the sheath.

In this example, the treatment device may be a balloon catheter. The left side view of FIG. 17(C) shows that the balloon catheter is stored inside the sheath in the first configuration in which the balloon is not inflated. The right side view of FIG. 17(C) shows that the balloon catheter is inflated when it is protruded from the sheath 2 so that the balloon catheter is able to perform the intended ERCP procedure.

Figure 17D:
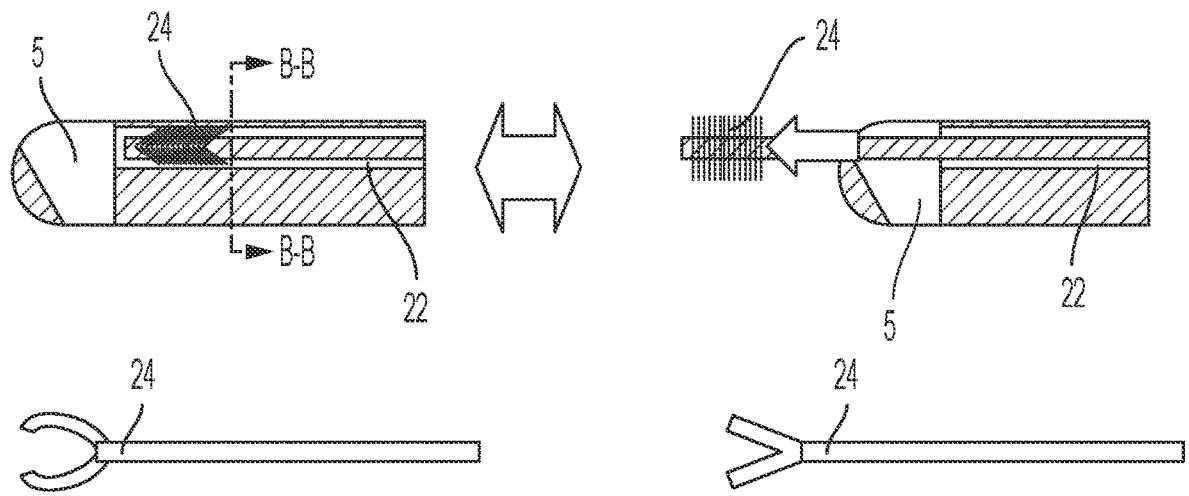

FIG. 17(D) shows two cross-sectional views of line A-A in FIG. 17(A) schematically illustrating side views of the guidewire holding device when still another example of the treatment device is stored inside the sheath 2 in the first configuration and then is switched into the second configuration in which the still another example of the treatment device is protruded from the sheath.

In this example, the treatment device may be a cytology brush. The left side view of FIG. 17(D) shows that the cytology brush is stored inside the sheath by shrinking its brushes in its first configuration. The right side view of FIG. 17(D) shows that the cytology brush is protruded from the sheath in its second configuration so that the cytology brush erects its brushes to perform the intended ERCP procedure. Also, as shown in 17(D), instead of the cytology brush, a biopsy forceps or a grasping forceps may also be used as the treatment device in this example. That is, the jaws of the biopsy forceps and the grasping forceps can be retracted when they are contained inside the sheath in their first configuration, and then opened when they are protruded from the sheath in their second configuration to perform the intended ERCP procedure.

Figure 17E:
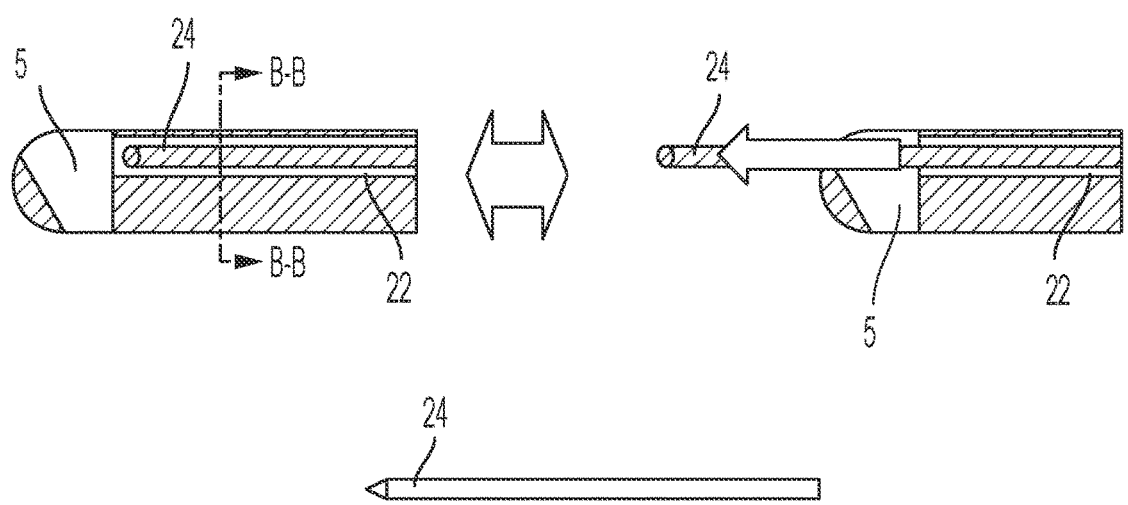

FIG. 17(E) shows two cross-sectional views of line A-A in FIG. 17(A) schematically illustrating side views of the guidewire holding device when still another example of the treatment device is stored inside the sheath 2 in the first configuration and then is switched into the second configuration in which the still another example of the treatment device 24 is protruded from the sheath.

In this example, the treatment device 24 may be a thin endoscope. The left side view of FIG. 17(E) shows that the thin endoscope is stored inside the sheath in its first configuration. The right side view of FIG. 17(E) shows that the thin endoscope is protruded from the sheath in its second configuration so that the thin endoscope can perform the intended ERCP procedure. Also, as shown in 17(E), instead of the thin endoscope, a puncture needle may also be used as the treatment device in this example. That is, the puncture needle is contained inside the sheath in its first configuration, and then is protruded from the sheath in their second configuration to perform the intended ERCP procedure.

The guidewire holding device according to the present invention is not limited to the examples of the above-described embodiments. In the following description, the same components as those already described will be assigned the same reference numerals and overlapping description will be omitted.

FIRST MODIFICATION OF THE FIRST EMBODIMENT

Figure 18A:
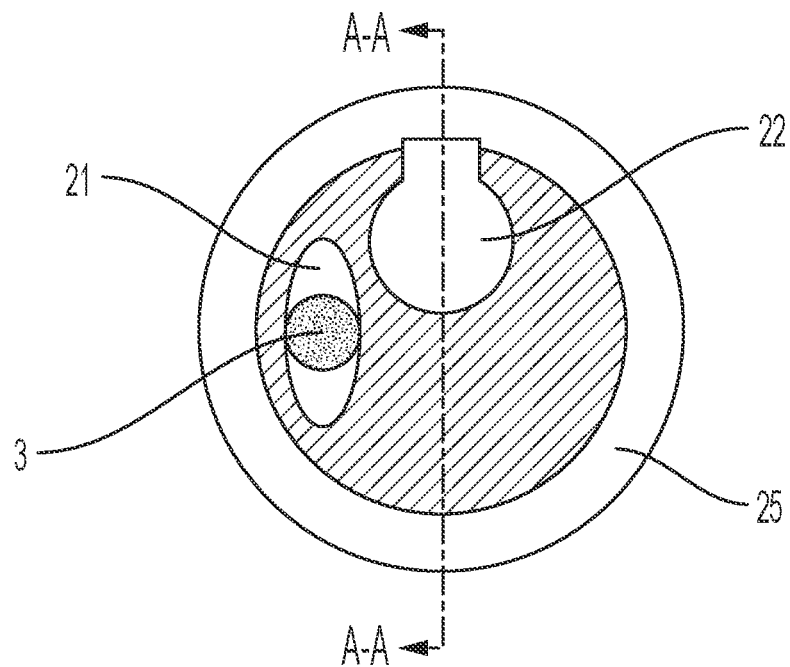
FIG. 18(A) is a cross-sectional view of line B-B in FIG. 18(B) schematically showing a front view of sheath.
Figure 18B:
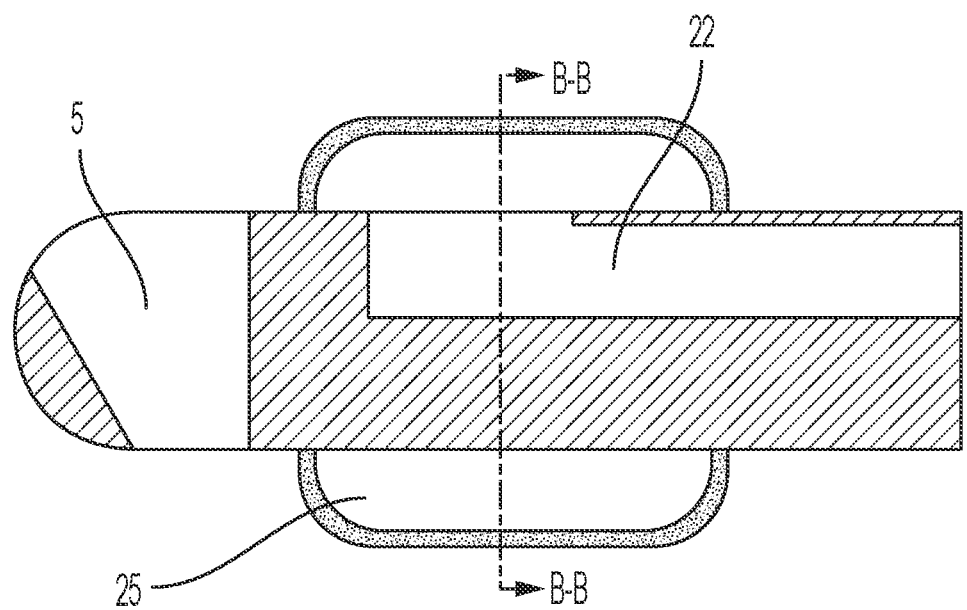
FIG. 18(B) shows a cross-sectional view of line A-A in FIG. 18(A) schematically illustrating side views of a guidewire holding device according to another exemplary embodiment.

FIG. 18(A) is a cross-sectional view of line B-B in FIG. 18(B) schematically showing a front view of sheath. FIG. 18(B) shows a cross-sectional view of line A-A in FIG. 18(A) schematically illustrating side views of the guidewire holding device including the treatment device that surrounds the sheath. In this modified embodiment, the treatment device may be a balloon that is fixed to and surrounds part of the distal end of the sheath. The second lumen of the sheath is an air delivery lumen that includes an opening inside the balloon. Before the guidewire holding device is inserted into the bile duct, the balloon is fixed to the distal end of the sheath in the first configuration in which the balloon is not inflated by the air delivery lumen. Once the guidewire holding device is inserted into the bile duct along with the guidewire GW, the balloon is switched into the second configuration in which the balloon is inflated via the opening by the air delivery lumen of the sheath, so as to perform the intended treatment.

SECOND MODIFICATION OF THE FIRST EMBODIMENT

Figure 19A:
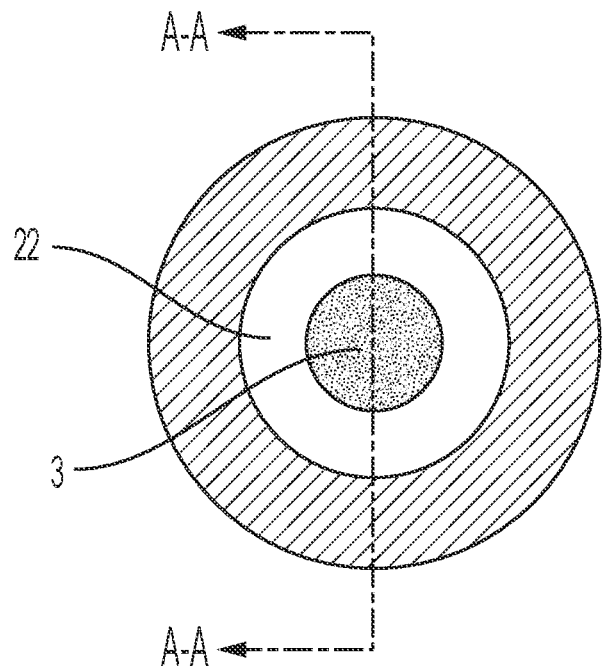
FIG. 19(A) is a cross-sectional view of line B-B in FIG. 19(B) schematically showing a front view of a sheath.
Figure 19B:
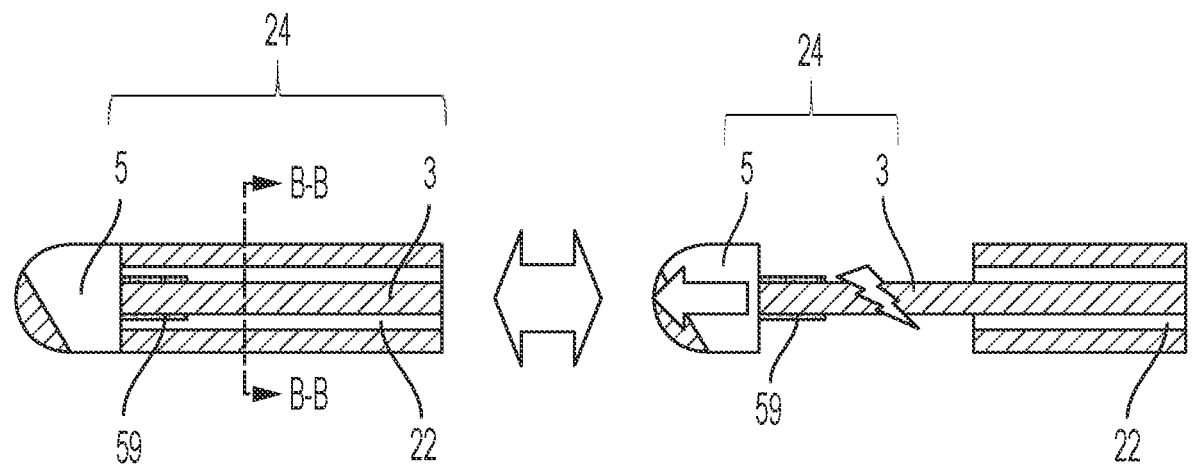
FIG. 19(B) shows a cross-sectional view of line A-A in FIG. 19(A) schematically illustrating side views of a guidewire holding device according to another exemplary embodiment.

FIG. 19(A) is a cross-sectional view of line B-B in FIG. 19(B) schematically showing a front view of sheath 2. FIG. 19(B) shows a cross-sectional view of line A-A in FIG. 19(A) schematically illustrating side views of the guidewire holding device 1 in which the hook and the operation wire serve as a treatment device. In this modified embodiment, the operation wire and the hook also serve as an electrode knife or a Diathermic dilator wire such that the operation wire is powered off in the first configuration when the hook is retracted back to the sheath 2, and is powered on in the second configuration when the operation wire pushes the hook to advance away from the sheath. In the situation of suing the electrode knife, the hook is made of an insulating material. In the situation of using the Diathermic dilator wire, the hook is made of a conductive material. Also, the distal end of the operation wire may be covered by the X-ray opaque material that serves to determine the position of the distal end of the treatment tool or the hook.

Figure 20A:
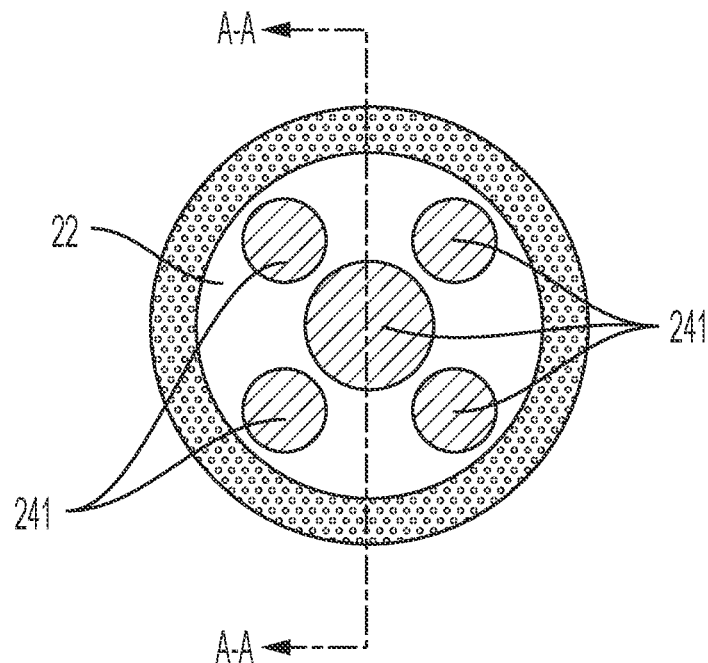
FIG. 20(A) is a cross-sectional view schematically showing a front view of a sheath.
Figure 20B:
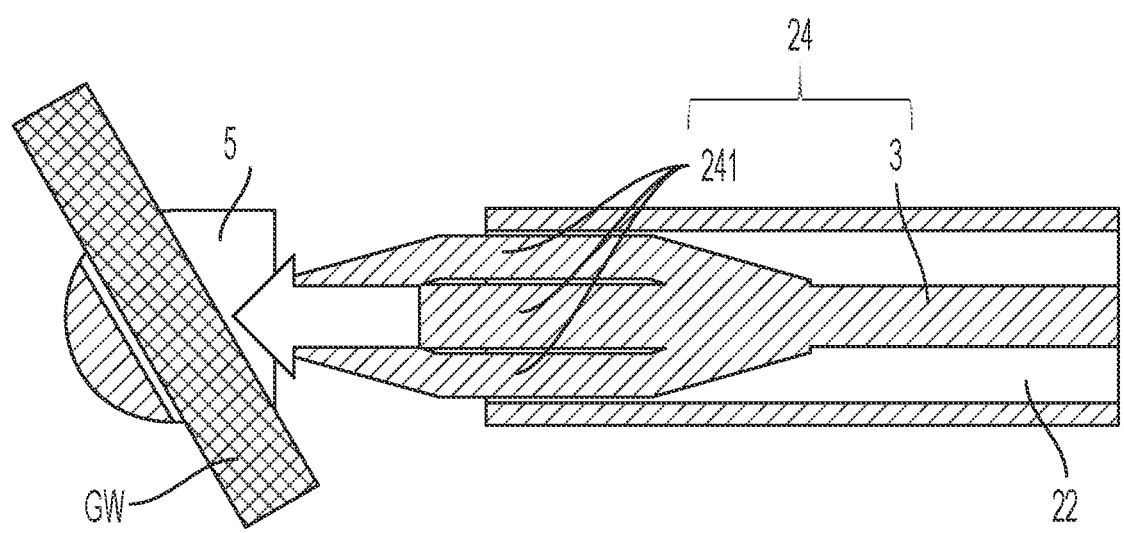
FIG. 20(B) shows a cross-sectional view of line A-A in FIG. 20(A) schematically illustrating a side view of a guidewire holding device.
Figure 20C:
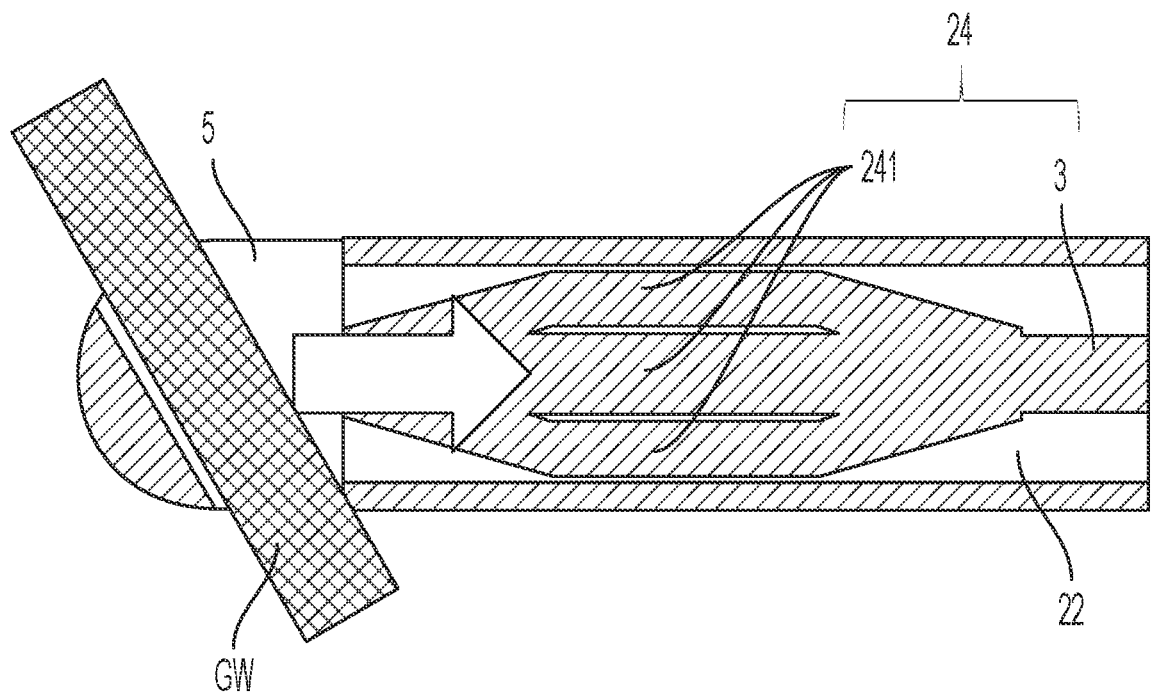
FIG. 20(C) shows a cross-sectional view of line A-A in FIG. 20(A) schematically illustrating another side view of the guidewire holding device.
Figure 20D:
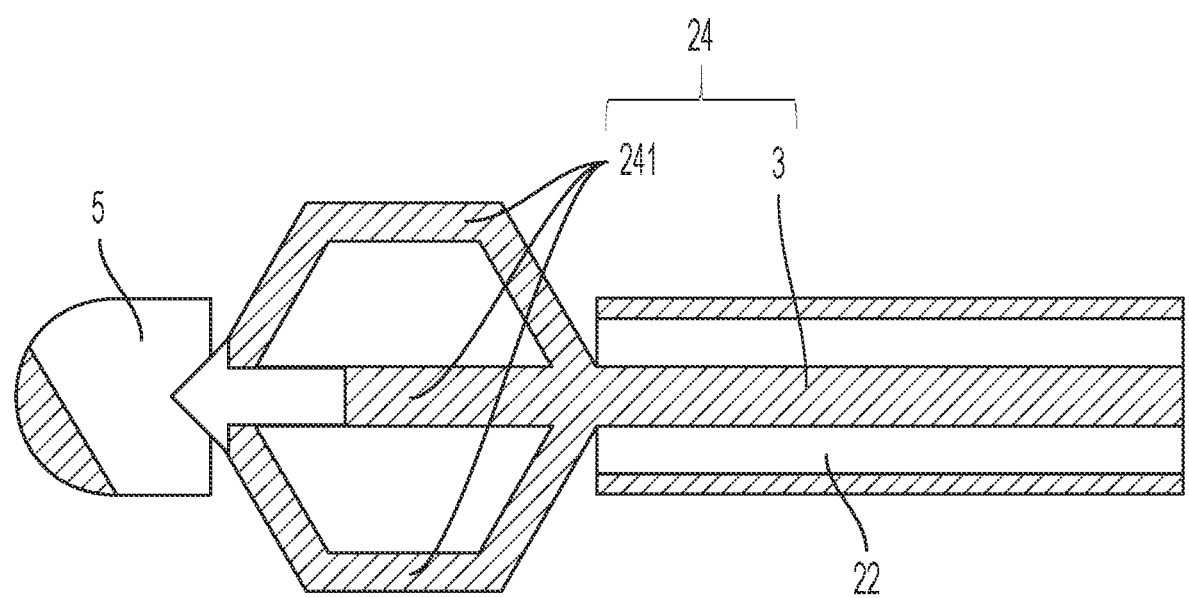
FIG. 20(D) shows a cross-sectional view of line A-A in FIG. 20(A) schematically illustrating still another side view of the guidewire holding device according to another exemplary embodiment.

FIG. 20(A) is a cross-sectional view schematically showing a front view of the sheath. FIG. 20(B) shows a cross-sectional view of line A-A in FIG. 20(A) schematically illustrating a side view of the guidewire holding device in which a basket wire is connected to the operation wire. FIG. 20(C) shows a cross-sectional view of line A-A in FIG. 20(A) schematically illustrating another side view of the guidewire holding device in which a basket wire is connected to the operation wire. FIG. 20(D) shows a cross-sectional view of line A-A in FIG. 20(A) schematically illustrating another side view of the guidewire holding device in which a basket wire is connected to the operation wire.

In this exemplary embodiment, inside the operation wire lumen, a basket wire (treatment tool) has one end connected to the operation wire and the other end connected to the hook. Thus, as shown in FIG. 20(B), the basket wire is arranged between the hook and the operation wire. The basket wire pushes the hook so that the hook advances to the advanced position to hook the guidewire GW. Once the guidewire is hooked on the hook, as shown in FIG. 20(C), the basket wire and the operation wire are pulled back so that the guidewire GW is captured and held between the hook and the sheath. The guidewire holding device is pushed into the bile duct along with the guidewire GW as described above. As shown in FIG. 20(D), once the basked wire is protrude from the sheath, it is opened so as to perform the intended ERCP procedure.

Although the present invention has been described in connection with the above exemplary embodiments, it will be appreciated by those skilled in the art that additions, deletions, modifications, and substitutions not specifically described may be made without department from the spirit and scope of the invention as defined in the appended claims.

What is claimed is:
1. A guidewire holding device, comprising:
 a sheath including a first lumen configured to receive a treatment tool;
 a holder detachably attached to a distal end of the sheath and including a slit extending from a distal end surface of the holder along a longitudinal axis of the sheath; and an operation wire connected to the holder, and configured to move the holder between a first configuration and a second configuration and to be inserted in a second lumen of the sheath,
wherein in the first configuration, the holder is spaced apart from the sheath in a longitudinal direction of the sheath, and
wherein in the second configuration, the holder contacts the sheath, and the holder and the sheath define a through hole.

2. The guidewire holding device according to claim 1, wherein the holder is configured to be switchable between holding a guidewire (GW) and releasing the guidewire, and wherein the slit is configured to have both the guidewire and the treatment tool pass therethrough with the treatment tool moving along and above the guidewire.

3. The guidewire holding device according to claim 1, wherein the slit is configured to have a width equal to or larger than a diameter of the first lumen.

4. The guidewire holding device according to claim 1, wherein the slit is configured to have a depth equal to or larger than a sum of a diameter of a guidewire and a diameter of the treatment tool.

5. The guidewire holding device according to claim 1, wherein, in a radial cross-section, when the holder is attached to the distal end of the sheath, an opening of the first lumen faces the slit, and the holder does not cover the opening of the first lumen.

6. The guidewire holding device according to claim 1, wherein the holder is configured to be connected to the treatment tool.

7. The guidewire holding device according to claim 6, wherein the treatment tool is inserted into the first lumen, and the treatment tool is powered on when the treatment tool is protruded from an opening of the first lumen.

8. The guidewire holding device according to claim 1, further comprising:
a basket connected to a proximal end of the holder, wherein the basket is configured to be inserted into the first lumen,
wherein the basket is closed in a third configuration, and is opened in a fourth configuration.

9. The guidewire holding device according to claim 1, further comprising a balloon mounted on an outer surface of the sheath and configured to be inflated,
wherein the sheath includes a second lumen, and the second lumen is configured to supply fluid to inside of the balloon.

10. The guidewire holding device according to claim 1, further comprising:
the treatment tool configured to be inserted into the first lumen, and
a wire connected to the treatment tool and configured to move the treatment tool between a third configuration and a fourth configuration,
wherein in the third configuration, the treatment tool is inserted in the first lumen,
wherein in the fourth configuration, a distal end side of the treatment tool protrudes from the first lumen,
wherein the holder is configured to be switchable between holding a guidewire and releasing the guidewire, and
wherein the slit is configured to have both the guidewire and the treatment tool pass therethrough with the treatment tool moving along and above the guidewire.

11. The guidewire holding device according to claim 1, further comprising a first guidewire configured to be held between the holder and the sheath,
wherein the held first guidewire is configured to guide the treatment tool.

12. The guidewire holding device according to claim 11, further comprising a second guidewire configured to be inserted into the first lumen and protruded from an opening of the first lumen,
wherein the held first guidewire is configured to guide the second guidewire protruded from the opening of the first lumen.

13. The guidewire holding device according to claim 1, wherein the operation wire is configured to prevent the holder from rotating relative to the sheath.

14. The guidewire holding device according to claim 1, wherein the holder includes an X-ray marker.

15. The guidewire holding device according to claim 1, wherein the slit includes a first slit opened toward a first direction, and wherein the sheath includes a second slit opened toward a second direction opposing the first direction.

16. The guidewire holding device according to claim 1, wherein the slit has a surface inclined relative to the longitudinal axis of the sheath.

17. An endoscope, comprising:
an operation unit,
an insertion portion located distally relative to the operation unit; and
the guidewire holding device according to claim 1, wherein the guide wire holding device is located at a distal end of the insertion portion.

18. A guidewire holding device, comprising:
a sheath including a lumen;
a holder disposed at a distal end of the sheath and configured to be switchable between holding a guidewire and releasing the guidewire;
a treatment tool inserted in the lumen to perform an intended treatment; and
a wire connected to the treatment tool and configured to move the treatment tool between a first configuration and a second configuration,
wherein, in the first configuration, the treatment tool is contained insider the lumen,
wherein, in the second configuration, the treatment tool is protruded from the distal end of the sheath, and
wherein the holder includes a slit, and wherein the slit is configured to have both the guidewire and the treatment tool pass therethrough with the treatment tool moving along and above the guidewire.

19. A guidewire holding device, comprising:
a sheath including a first lumen configured to receive a treatment tool, wherein the treatment tool is configured to be inserted into the first lumen;
a holder detachably attached to a distal end of the sheath and including a slit extending from a distal end surface of the holder along a longitudinal axis of the sheath; and
a wire connected to the treatment tool and configured to move the treatment tool between a first configuration and a second configuration,
wherein in the first configuration, the treatment tool is inserted in the first lumen,
wherein in the second configuration, a distal end side of the treatment tool protrudes from the first lumen,
wherein the holder is configured to be switchable between holding a guidewire and releasing the guidewire, and wherein the slit is configured to have both the guidewire and the treatment tool pass therethrough with the treatment tool moving along and above the guidewire.

* * * * *